(12) United States Patent
Bressler et al.

(10) Patent No.: US 11,819,578 B2
(45) Date of Patent: Nov. 21, 2023

(54) NANOFIBER SCAFFOLDS

(71) Applicants: Trustees of Boston University, Boston, MA (US); The General Hospital Corporation, Boston, MA (US)

(72) Inventors: Eric M. Bressler, Allston, MA (US); Sarah Adams, Brighton, MA (US); Yolonda Colson, Dover, MA (US); Mark W. Grinstaff, Brookline, MA (US); Wilson Wai Chun Wong, Brookline, MA (US)

(73) Assignees: Trustees of Boston University, Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 17/962,149

(22) Filed: Oct. 7, 2022

(65) Prior Publication Data
US 2023/0114205 A1    Apr. 13, 2023

Related U.S. Application Data

(60) Provisional application No. 63/253,206, filed on Oct. 7, 2021.

(51) Int. Cl.
*A61K 9/70* (2006.01)
*A61K 47/36* (2006.01)
*A61K 47/10* (2017.01)
*A61K 47/64* (2017.01)
*A61K 47/34* (2017.01)

(52) U.S. Cl.
CPC ............... *A61K 9/70* (2013.01); *A61K 47/10* (2013.01); *A61K 47/34* (2013.01); *A61K 47/36* (2013.01); *A61K 47/64* (2017.08)

(58) Field of Classification Search
CPC .......... A61K 9/70; A61K 47/64; A61K 47/10; A61K 47/34; A61K 47/36
See application file for complete search history.

(56) References Cited

U.S. PATENT DOCUMENTS

| 7,235,295 B2 | 6/2007 | Laurencin et al. |
| 10,251,841 B2 | 4/2019 | Grinstaff et al. |
| 2013/0195954 A1 | 8/2013 | Colson et al. |
| 2013/0209537 A1 | 8/2013 | Fu-Giles |
| 2015/0037375 A1 | 2/2015 | Grinstaff et al. |
| 2018/0346541 A1 | 12/2018 | Wong et al. |
| 2020/0046883 A1 | 2/2020 | Martin et al. |
| 2020/0069846 A1 | 3/2020 | Martin et al. |

FOREIGN PATENT DOCUMENTS

WO    2020159946 A1    8/2020

OTHER PUBLICATIONS

Balijepalli et al., Poly-Amido-Saccharides (PASs): Functional Synthetic Carbohydrate Polymers Inspired by Nature. Acc. Chem. Res. 2020, 53, 2167-2179 (Year: 2020).*
Chen et al. "Emerging Roles of Electrospun Nanofibers in Cancer Research." Advanced healthcare materials vol. 7,6: e1701024 (2018).
Monterrubio et al. "SN-38-loaded nanofiber matrices for local control of pediatric solid tumors after subtotal resection surgery." Biomaterials 79 (2016).
Smith et al. "Biopolymers codelivering engineered T cells and STING agonists can eliminate heterogeneous tumors." The Journal of clinical investigation 127.6: 2176-2191 (2017).
Stoddard et al. "In pursuit of functional electrospun materials for clinical applications in humans." Therapeutic delivery vol. 7,6: 387-409 (2016).
International Search Report and Written Opinion dated Dec. 30, 2022 in PCT/US2022/046026.
Liechty et al. "Polymers for drug delivery systems." Annual review of chemical and biomolecular engineering 1 (2010): 149.

* cited by examiner

*Primary Examiner* — Robert A Wax
*Assistant Examiner* — Olga V. Tcherkasskaya
(74) *Attorney, Agent, or Firm* — Nixon Peabody LLP; Ronald I. Eisenstein; Ravinderjit Braich

(57) ABSTRACT

The present disclosure generally relates to compositions and method for delivery, e.g., sustained delivery of active agents, and their use for the treatment of diseases or disorders.

30 Claims, 19 Drawing Sheets

NANOFIBER SCAFFOLDS

CROSS-REFERENCE TO RELATED APPLICATIONS

This application claims benefit under 35 U.S.C. § 119(e) of the U.S. Provisional Application No. 63/253,206, filed Oct. 7, 2021, the contents of which are incorporated herein by reference in their entirety.

GOVERNMENT SUPPORT

This invention was made with government support under Contract No. CA232708 awarded by the National Institutes of Health. The government has certain rights in the invention.

TECHNICAL FIELD

The present disclosure relates to compositions and methods for delivery, e.g., sustained delivery of active agents.

BACKGROUND

There is a need in the art for delivering molecules, e.g., a therapeutic agent, to a desired location over a period of time. The present disclosure addresses some of these needs.

SUMMARY

In one aspect provided herein is a drug delivery composition. The drug delivery composition comprises scaffold and an active agent. The scaffold is prepared from nanofibers, e.g., electronspun nanofibers of a first polymer and comprises a plurality of pores. In some embodiments of any one of the aspects described herein, the active agent is in a mixture comprising the active agent, a second polymer and a third polymer, and wherein the mixture is present in the pores of the scaffold. In some embodiments of any one of the aspects described herein, the active agent, without being in a mixture with the second and third polymer, is distributed inside the nanofibers or adsorbed on the nanofibers.

In some embodiments of any one of the aspects described herein, the first and second polymers are different. For example, the first polymer is hydrophobic and the second polymer is hydrophilic. In some embodiments of any one of the aspects described herein, the second and third polymer are different. For example, the second polymer is hydrophilic, and the third polymer is a copolymer, e.g., a copolymer comprising a hydrophilic portion and a hydrophobic portion. In some embodiments of any one of the aspects described herein, the first polymer, the second polymer and the third polymer, are different. For example, the first polymer is hydrophobic, the second polymer is hydrophilic, and the third polymer is amphiphilic.

In some embodiments of any one of the aspects described herein, the active agent is comprised in a particle. The active agent in the mixture with the second and third polymer can be comprised in a particle. It is noted, additional components can be added to form the particle. Accordingly, in some embodiments of any one of the aspects described herein, the particle comprises the active agent, the second polymer, the third polymer, and a fourth polymer. Usually, the fourth polymer is different from the first, the second and/or the third polymer. Exemplary polymers for use as the fourth polymer include, but are not limited to polyamidosaccharides.

In some embodiments of any one of the aspects described herein, the active agent is present in a mixture comprising the active agent, a second polymer and a third polymer, and wherein the first polymer is polycaprolactone; the second polymer is chitosan; and the third polymer is poloxamer 407, sold under the tradename PLURONIC® F-127.

In some embodiments of any one of the aspects described herein, the active agent is hydrophobic. In some other embodiments of any one of the aspects described herein, the active agent is hydrophilic.

In some embodiments of any one of the aspects described herein, the active agent is a therapeutic agent. For example, the active agent is selected from the group consisting of anti-cancer agents, anti-inflammatory agents, antibiotic agents or antibacterial agents, anti-proliferatives, anti-migratory agents, anti-fibrotic agents, pro-apoptotics, anti-neoplastics, immuno-suppressants, wound repairing agents, and skin ameliorating agents.

In some embodiments of any one of the aspects described herein, the active agent is conjugated with a targeting ligand.

In some embodiments of any one of the aspects described herein, the active agent is a chimeric antigen receptor. For example, the active agent is a multi-component chimeric antigen receptor comprising: (a) a target binding domain (e.g., an antibody reagent specific for a first target ligand) and a first interaction domain (e.g., a protein interaction domain); and (b) a first signaling domain capable of binding specifically with the first interaction domain (e.g., a signaling polypeptide comprising an extracellular protein interaction domain that can bind specifically with the protein interaction domain), and a second signaling domain (e.g., an intracellular T cell receptor (TCR) signaling domain). Exemplary multi-component chimeric antigen receptors are described, for example, in US patent publication US20180346541, content of which is incorporated herein by reference in its entirety. Such, multi-component chimeric antigen receptors are also referred to as zipFV.

In some embodiments of any one of the aspects described herein, the active agent is an imagining agent.

Without wishing to be bound by a theory, the drug delivery composition described herein can provide sustained release of the active agent. Accordingly, in another aspect, provided herein is a method for delivering an active agent to a cell. The method comprises contacting the drug delivery composition described herein with the cell.

In another aspect, provided herein is a method for activating an inducible chimeric antigen receptor (CAR) T cell. The method comprises contacting an inducible CAR T cells with a drug delivery composition described herein. In some embodiments, the method comprises contacting an inducible CAR T cells with a drug delivery composition described herein, and wherein the active agent is zipFV.

DETAILED DESCRIPTION OF THE INVENTION

Figure 1:
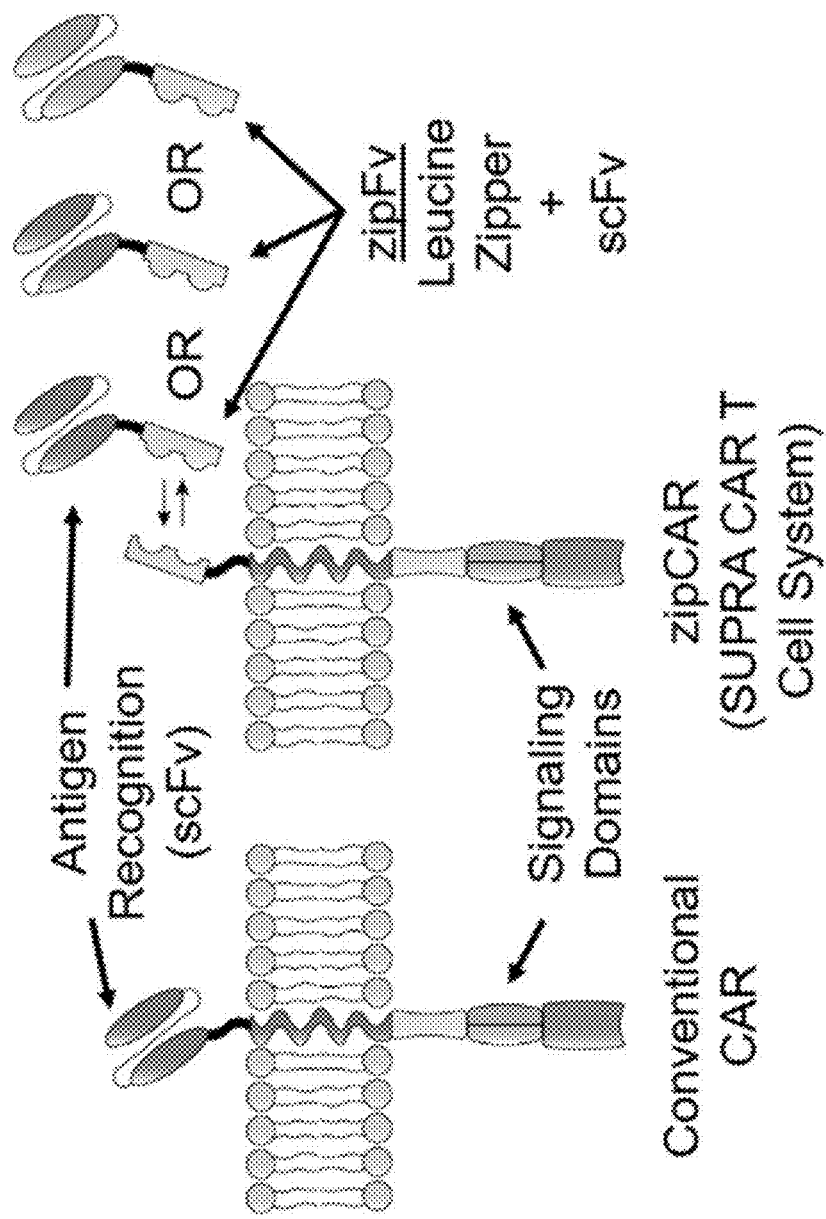
FIG. 1 depicts conventional vs. CARs with variable-affinity leucine zipper (zipCAR). The SUPRA system utilizes zipCARs to bind a zipFv to its cognate zipper expressed on the cell surface. This allows for logic gates and response tuning (shown: OR gate).

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

The drug delivery composition described herein can provide sustained release of the active agent. The term "sustained release" means that the active agent is released over an extended period of time from the drug delivery composition. For example, the active agent is released from the drug delivery composition at such a rate that the target environment concentrations (levels), e.g., an effective amount of the active agent, are maintained for an extended period of time. Accordingly, in some embodiments of any one of the aspects described herein, the active agent is released over a period of at least one day, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, twenty-nine days, thirty days, thirty-one days, thirty-two days, thirty-three days, thirty-four days, thirty-five days, thirty-six days, thirty-seven days, thirty-eight days, thirty-nine days, forty days, forty-one days, forty-two days, forty-three days, forty-four days, forty-five days, forty-six days, forty-seven days, forty-eight days, forty-nine days, fifty days, fifty-one days, fifty-two days, fifty-three days, fifty-four days, fifty-five days, fifty-six days, fifty-seven days, fifty-eight days, fifty-nine days, sixty days, sixty-one days, sixty-two days, sixty-three days, sixty-four days, sixty-five days, sixty-six days, sixty-seven days, sixty-eight days, sixty-nine days, seventy days, seventy-one days, seventy-two days, seventy-three days, seventy-four days, seventy-five days, seventy-six days, seventy-seven days, seventy-eight days, seventy-nine days, eighty days, eighty-one days, eighty-two days, eighty-three days, eighty-four days, eighty-five days, eighty-six days, eighty-seven days, eighty-eight days, eighty-nine days, ninety days, ninety-one days, ninety-two days, ninety-three days, ninety-four days, ninety-five days, ninety-six days, ninety-seven days, ninety-eight days, ninety-nine days, one hundred days, one hundred and one day, one hundred and two days, one hundred and three days, one hundred and four days, one hundred and five days, one hundred and six days, one hundred and seven days, one hundred and eight days, one hundred and nine days, one hundred and ten days, one hundred and eleven days, one hundred and twelve days, one hundred and thirteen days, one hundred and fourteen days, one hundred and fifteen days, one hundred and sixteen days, one hundred and seventeen days, one hundred and eighteen days, one hundred and nineteen days, one hundred and twenty days, one hundred and twenty-one days, one hundred and twenty-two days, one hundred and twenty-three days, one hundred and twenty-four days, one hundred and twenty-five days, one hundred and twenty-six days, one hundred and twenty-seven days, one hundred and twenty-eight days, one hundred and twenty-nine days, one hundred and thirty days, one hundred and thirty-one days, one hundred and thirty-two days, one hundred and thirty-three days, one hundred and thirty-four days, one hundred and thirty-five days, one hundred and thirty-six days, one hundred and thirty-seven days, one hundred and thirty-eight days, one hundred and thirty-nine days, one hundred and forty days, one hundred and forty-one days, one hundred and forty-two days, one hundred and forty-three days, one hundred and forty-four days, one hundred and forty-five days, one hundred and forty-six days, one hundred and forty-seven days, one hundred and forty-eight days, one hundred and forty-nine days, one hundred and fifty days, one hundred and fifty-one days, one hundred and fifty-two days, one hundred and fifty-three days, one hundred and fitly-four days, one hundred and fifty-five days, one hundred and fifty-six days, one hundred and fifty-seven days, one hundred and fifty-eight days, one hundred and fifty-nine days, one hundred and sixty days, one hundred and sixty-one days, one hundred and sixty-two days, one hundred and sixty-three days, one hundred and sixty-four days, one hundred and sixty-five days, one hundred and sixty-six days, one hundred and sixty-seven days, one hundred and sixty-eight days, one hundred and sixty-nine days, one hundred and seventy days, one hundred and seventy-one days, one hundred and seventy-two days, one hundred and seventy-three days, one hundred and seventy-four days, one hundred and seventy-five days, one hundred and seventy-six days, one hundred and seventy-seven days, one hundred and seventy-eight days, one hundred and seventy-nine days, one hundred and eighty days, one hundred and eighty-one days, one hundred and eighty-two days, one hundred and eighty-three days, one hundred and eighty-four days, one hundred and eighty-five days, one hundred and eighty-six days, one hundred and eighty-seven days, one hundred and eighty-eight days, one hundred and eighty-nine days, one hundred and ninety days, one hundred and ninety-one days, one hundred and ninety-two days, one hundred and ninety-three days, one hundred and ninety-four days, one hundred and ninety-five days, one hundred and ninety-six days, one hundred and ninety-seven days, one hundred and ninety-eight days, one hundred and ninety-nine days, two hundred days or more.

In some embodiments of any one of the aspects, less than 5% of the active material incorporated into the drug delivery composition is released in one day. For example, less than 10% of the active agent is released in one day, less than 15% of the active agent is released in one day, less than 20% of the active agent is released in one day, less than 25% of the active agent is released in one day, less than 30% of the active agent is released in one day, less than 35% of the active agent is released in one day, less than 40% of the active agent is released in one day, less than 45% of the active agent is released in one day, less than 50% of the active agent is released in one day, less than 55% of the active agent is released in one day, less than 60% of the active agent is released in one day, less than 65% of the active agent is released in one day, less than 70% of the active agent is released in one day, less than 75% or more of the active agent is released in one day.

In some embodiments, the drug delivery composition releases an effective amount of the active agent for a period of at least one day, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, twenty-nine days, thirty days, thirty-one days, thirty-two days, thirty-three days, thirty-four days, thirty-five days, thirty-six days, thirty-seven days, thirty-eight days, thirty-nine days, forty days, forty-one days, forty-two days, forty-three days, forty-four days, forty-five days, forty-six days, forty-seven days, forty-eight days, forty-nine days, fifty days, fifty-one days, fifty-two days, fifty-three days, fifty-four days, fifty-five days, fifty-six days, fifty-seven days, fifty-eight days, fifty-nine days, sixty days, sixty-one days, sixty-two days, sixty-three days, sixty-four days, sixty-five days, sixty-six days, sixty-seven days, sixty-eight days, sixty-nine days, seventy days, seventy-one days, seventy-two days, seventy-three days, seventy-four days, seventy-five days, seventy-six days, seventy-seven days, seventy-eight days, seventy-nine days, eighty days, eighty-one days, eighty-two days, eighty-three days, eighty-four days, eighty-five days, eighty-six days, eighty-seven days, eighty-eight days, eighty-nine days, ninety days, ninety-one days, ninety-two days, ninety-three days, ninety-four days, ninety-five days, ninety-six days, ninety-seven days, ninety-eight days, ninety-nine days, one hundred days, one hundred and one day, one hundred and two days, one hundred and three days, one hundred and four days, one hundred and five days, one hundred and six days, one hundred and seven days, one hundred and eight days, one hundred and nine days, one hundred and ten days, one hundred and eleven days, one hundred and twelve days, one hundred and thirteen days, one hundred and fourteen days, one hundred and fifteen days, one hundred and sixteen days, one hundred and seventeen days, one hundred and eighteen days, one hundred and nineteen days, one hundred and twenty days, one hundred and twenty-one days, one hundred and twenty-two days, one hundred and twenty-three days, one hundred and twenty-four days, one hundred and twenty-five days, one hundred and twenty-six days, one hundred and twenty-seven days, one hundred and twenty-eight days, one hundred and twenty-nine days, one hundred and thirty days, one hundred and thirty-one days, one hundred and thirty-two days, one hundred and thirty-three days, one hundred and thirty-four days, one hundred and thirty-five days, one hundred and thirty-six days, one hundred and thirty-seven days, one hundred and thirty-eight days, one hundred and thirty-nine days, one hundred and forty days, one hundred and forty-one days, one hundred and forty-two days, one hundred and forty-three days, one hundred and forty-four days, one hundred and forty-five days, one hundred and forty-six days, one hundred and forty-seven days, one hundred and forty-eight days, one hundred and forty-nine days, one hundred and fifty days, one hundred and fifty-one days, one hundred and fifty-two days, one hundred and fifty-three days, one hundred and fifty-four days, one hundred and fifty-five days, one hundred and fifty-six days, one hundred and fifty-seven days, one hundred and fifty-eight days, one hundred and fifty-nine days, one hundred and sixty days, one hundred and sixty-one days, one hundred and sixty-two days, one hundred and sixty-three days, one hundred and sixty-four days, one hundred and sixty-five days, one hundred and sixty-six days, one hundred and sixty-seven days, one hundred and sixty-eight days, one hundred and sixty-nine days, one hundred and seventy days, one hundred and seventy-one days, one hundred and seventy-two days, one hundred and seventy-three days, one hundred and seventy-four days, one hundred and seventy-five days, one hundred and seventy-six days, one hundred and seventy-seven days, one hundred and seventy-eight days, one hundred and seventy-nine days, one hundred and eighty days, one hundred and eighty-one days, one hundred and eighty-two days, one hundred and eighty-three days, one hundred and eighty-four days, one hundred and eighty-five days, one hundred and eighty-six days, one hundred and eighty-seven days, one hundred and eighty-eight days, one hundred and eighty-nine days, one hundred and ninety days, one hundred and ninety-one days, one hundred and ninety-two days, one hundred and ninety-three days, one hundred and ninety-four days, one hundred and ninety-five days, one hundred and ninety-six days, one hundred and ninety-seven days, one hundred and ninety-eight days, one hundred and ninety-nine days, two hundred days or more.

The phrase "effective amount" as used herein means that amount of an active agent which is effective to achieve a desired result. For example, when the active agent is a therapeutic agent, the effective amount is an amount which is effective for producing some desired therapeutic effect in at least a sub-population of cells in a model organism or subject at a reasonable benefit/risk ratio applicable to any medical treatment. Effective amounts, toxicity, and therapeutic efficacy of active agents can be determined by standard pharmaceutical procedures in cell cultures or experimental animals, e.g., for determining the lethal dose, 50% (LD50) (the dose lethal to 50% of the population) and the effective dose, 50% (ED50) (the dose therapeutically effective in 50% of the population). A therapeutically effective dose can be estimated initially from cell culture assays. Also, a dose can be formulated in animal models to achieve a circulating plasma concentration range that includes the half-maximal inhibitory concentration (IC50) (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size or growth, among others. The dosage can be determined by a physician and adjusted, as necessary, to suit observed effects of the treatment.

An effective amount of the active agent can be a release rate of from about 1 ng of the active/day to about 5 µg of the active agent/day. For example, an effective amount effective amount of the active agent can be a release rate of from about 2.5 ng of the active/day to about 2.5 µg of the active agent/day, from about 5 ng of the active/day to about 2 µg of the active agent/day, or from about 10 ng of the active/day to about 1.5 µg of the active agent/day, or from about 15 ng of the active/day to about 1 µg of the active agent/day, or from about 20 ng of the active/day to about 0.75 µg of the active agent/day, or from about 25 ng of the active/day to about 0.5 µg of the active agent/day, or from about 50 ng of the active/day to about 0.25 µg of the active agent/day, or from about 75 ng of the active/day to about 0.1 µg of the active agent/day.

When the active agent is comprised in particles, e.g., nanoparticles, the particles can be released over one day, over two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, twenty-nine days, thirty days, thirty-one days, thirty-two days, thirty-three days, thirty-four days, thirty-five days, thirty-six days, thirty-seven days, thirty-eight days, thirty-nine days, forty days, forty-one days, forty-two days, forty-three days, forty-four days, forty-five days, forty-six days, forty-seven days, forty-eight days, forty-nine days, fifty days, fifty-one days, fifty-two days, fifty-three days, fifty-four days, fifty-five days, fifty-six days, fifty-seven days, fifty-eight days, fifty-nine days, sixty days, sixty-one days, sixty-two days, sixty-three days, sixty-four days, sixty-five days, sixty-six days, sixty-seven days, sixty-eight days, sixty-nine days, seventy days, seventy-one days, seventy-two days, seventy-three days, seventy-four days, seventy-five days, seventy-six days, seventy-seven days, seventy-eight days, seventy-nine days, eighty days, eighty-one days, eighty-two days, eighty-three days, eighty-four days, eighty-five days, eighty-six days, eighty-seven days, eighty-eight days, eighty-nine days, ninety days, ninety-one days, ninety-two days, ninety-three days, ninety-four days, ninety-five days, ninety-six days, ninety-seven days, ninety-eight days, ninety-nine days, one hundred days, one hundred and one day, one hundred and two days, one hundred and three days, one hundred and four days, one hundred and five days, one hundred and six days, one hundred and seven days, one hundred and eight days, one hundred and nine days, one hundred and ten days, one hundred and eleven days, one hundred and twelve days, one hundred and thirteen days, one hundred and fourteen days, one hundred and fifteen days, one hundred and sixteen days, one hundred and seventeen days, one hundred and eighteen days, one hundred and nineteen days, one hundred and twenty days, one hundred and twenty-one days, one hundred and twenty-two days, one hundred and twenty-three days, one hundred and twenty-four days, one hundred and twenty-five days, one hundred and twenty-six days, one hundred and twenty-seven days, one hundred and twenty-eight days, one hundred and twenty-nine days, one hundred and thirty days, one hundred and thirty-one days, one hundred and thirty-two days, one hundred and thirty-three days, one hundred and thirty-four days, one hundred and thirty-five days, one hundred and thirty-six days, one hundred and thirty-seven days, one hundred and thirty-eight days, one hundred and thirty-nine days, one hundred and forty days, one hundred and forty-one days, one hundred and forty-two days, one hundred and forty-three days, one hundred and forty-four days, one hundred and forty-five days, one hundred and forty-six days, one hundred and forty-seven days, one hundred and forty-eight days, one hundred and forty-nine days, one hundred and fifty days, one hundred and fifty-one days, one hundred and fifty-two days, one hundred and fifty-three days, one hundred and fifty-four days, one hundred and fifty-five days, one hundred and fifty-six days, one hundred and fifty-seven days, one hundred and fifty-eight days, one hundred and fifty-nine days, one hundred and sixty days, one hundred and sixty-one days, one hundred and sixty-two days, one hundred and sixty-three days, one hundred and sixty-four days, one hundred and sixty-five days, one hundred and sixty-six days, one hundred and sixty-seven days, one hundred and sixty-eight days, one hundred and sixty-nine days, one hundred and seventy days, one hundred and seventy-one days, one hundred and seventy-two days, one hundred and seventy-three days, one hundred and seventy-four days, one hundred and seventy-five days, one hundred and seventy-six days, one hundred and seventy-seven days, one hundred and seventy-eight days, one hundred and seventy-nine days, one hundred and eighty days, one hundred and eighty-one days, one hundred and eighty-two days, one hundred and eighty-three days, one hundred and eighty-four days, one hundred and eighty-five days, one hundred and eighty-six days, one hundred and eighty-seven days, one hundred and eighty-eight days, one hundred and eighty-nine days, one hundred and ninety days, one hundred and ninety-one days, one hundred and ninety-two days, one hundred and ninety-three days, one hundred and ninety-four days, one hundred and ninety-five days, one hundred and ninety-six days, one hundred and ninety-seven days, one hundred and ninety-eight days, one hundred and ninety-nine days, two hundred days or more.

In some embodiments of any one of the aspects described herein, the amount of the active agent, e.g., zipFv released can be at least 250 ng, at least 300 ng, at least 350 ng, at least 400 ng, at least 450 ng, at least 500 ng, at least 550 ng, at least 600 ng, at least 650 ng, at least 700 ng, at least 750 ng, at least 800 ng, at least 850 ng, at least 900 ng, at least 950 ng, at least 1000 ng, at least 1050 ng, at least 1100 ng, at least 1150 ng, at least 1200 ng, at least 1250 ng, at least 1300 ng, at least 1350 ng, at least 1400 ng, at least 1450 ng, at least 1500 ng, at least 1550 ng, at least 1600 ng, at least 1650 ng, at least 1700 ng, at least 1750 ng, at least 1800 ng, at least 1850 ng, at least 1900 ng, at least 1950 ng, at least 2000 ng or more.

In some embodiments of any one of the aspects described herein, the composition exhibits tunable drug release. As used herein, "tunable drug release" refers to the ability to reduce either the cumulative amount of released drug over a fixed time period by at least 10%, e.g., 15%, 20%, 25%, 30% or more, or the ability to alter the rate of drug release over a fixed time period by at least 10%, e.g., 15%, 20%, 25%, 30% or more, or both.

In some embodiments of any one of the aspects described herein, the active agent is released from the composition with linear or first order kinetics.

Embodiments of the various aspects described herein include a scaffold. As used herein, the term "scaffold" refers to a material that provides a supporting framework to the overall drug delivery composition. The scaffold can be in any desired different form, shape or size. For example, the scaffold can be in the form of a mesh, fibrous mats, a film, pellets, droplets, beads, or more complex structures (e.g., tubes, implants etc.).

The fibers comprised in the scaffold can have an average diameter between about 10 nm to about 500 nm. For example, the fibers comprising the scaffold can have an average diameter between about 25 nm to about 250 nm, between about 50 nm to about 200 nm, between from about 75 nm to about 150 nm, or between about 100 nm to about 125 nm. In some embodiments of any one of the aspects described herein, the fibers comprising the scaffold can have an average diameter of about 100 nm or about 125 nm.

In some embodiments, the scaffold is in form of a mesh. As used herein, the term "mesh" refers to a multidimensional structure that has a large number of closely-spaced holes or pores, which is composed of a plurality of elongated and interconnected elements, such as nanofibers. In some embodiments of any one of the aspects described herein, the scaffold is in form of a non-woven mesh. As used herein, the term "non-woven mesh" refers to a mesh that has a structure of individual fibers or filaments, e.g., nanofibers, which are interspersed, but not in a repeating pattern that can be identified.

In some embodiments, the composition comprises a non-woven mesh form factor with an average thickness between about 0.5 to about 1000 μm. For example, the composition comprises a non-woven mesh form factor with an average thickness between about 0.5 to about 750 μm, thickness between about 0.5 to about 500 μm, or thickness between about 0.5 to about 250 μm.

The scaffold can be manufactured using e.g., electro spraying, electrospinning, ultrasonic spraying, dip-coating, vapor deposition, spin-coating, knife-coating, melt-coating, or injection molding. In some embodiments of any one of the aspects described herein, the scaffold is an electrospun nanofiber mesh. Electrospinning is a processing technique where a polymer can be shaped into fibers that can range in diameters on the order of nanometers to micrometers. A polymer is either dissolved or melted so that it becomes a viscous fluid. The polymer fluid is then loaded into a syringe that can pump the solution out at a controlled rate. The syringe is supplied with a high voltage, and is aimed at a grounded collector. The high voltage combined with the grounded collector creates a strong electric field which exerts a force on the polymer fluid. Because the electrostatic force is strongest at the tip of the needle of the syringe, a thin ribbon of polymer is pulled off of the tip. As the ribbon flies through the air ejecting solvent, it separates into even smaller fibers that eventually collide and collect with the grounded collector, leaving a mat of nanometer to micrometer diameter fibers.

In some embodiments of any one of the aspects described herein, the scaffold comprises at least one pore having a pore size of e.g., between 0.01 microns to 100 microns, between 0.1 microns to 100 microns, between 0.1 microns to 50 microns, between 0.1 microns to 10 microns, between 0.1 microns to 5 microns, between 0.1 microns to 2 microns, between 0.2 microns to 1.5 microns in another embodiment, the pore size can be non-uniform. In another embodiment, the pore size can be uniform.

Embodiments of the various aspects described herein include a polymer. The term "polymer" is well known to those of skill in the art, and broadly includes a macromolecule comprising polymerized monomers of the same or different types. The term "polymer" includes, but is not limited to, homopolymers, copolymers, such as for example, block, graft, random and alternating copolymers, terpolymers, etc. Furthermore, unless otherwise specifically limited, the term "polymer" includes all possible geometrical configurations of the molecule. These configurations include, but are not limited to isotactic, syndiotactic and random symmetries. As used herein, the term "polymer" encompasses synthetic and natural polymers made from any suitable monomers.

In some embodiments of any one of the aspects described herein, the polymer is hydrophobic, e.g., a hydrophobic polymer. The term "hydrophobic polymer" is well known to those of skill in the art, and broadly includes a polymer having a solubility in water at 25° C. of less than 1% by weight. Exemplary hydrophobic polymers include, but are not limited to hydrocarbon polymers and/or co-polymers, aromatic polyurethanes, silicone rubber, polysiloxanes, polycaprolactone (PCL), polycarbonate, poly-L-lactide (PLLA), poly-D,L-lactide (PDLLA), poly-DL-glycolide, poly-D,L-lactic-co-glycolic acid (PLGA), poly-delta-verolactone (PVL), and polyL-histadine (pHis) polyetheretherketone (PEEK), polyamide, polyimide, polyvinyl acetate, polyvinylchloride, polyethylene, alkyl cellulose, ethyl cellulose, polymethacrylate-based copolymer (EUDRAGIT®), waxes, polyesters, polyanhydrides, combinations thereof, and others known to those skilled in the art.

In some embodiments of any one of the aspects described herein, the hydrophobic polymer is polycaprolactone. For example, the polymer of the scaffold, e.g., the first polymer, is PCL.

In some embodiments of any one of the aspects described herein, the polymer is hydrophilic, e.g., a hydrophilic polymer. The term "hydrophilic polymer" is well known to those of skill in the art, and broadly includes polymers that have affinity for water and tend to be soluble in aqueous and polar solvents such as alcohols (e.g., methanol, ethanol, propanol, and isopropanol). Generally, hydrophilic polymers contain polar or charged functional groups, rendering them soluble in water. In some embodiments of any one of the aspects described herein, a hydrophilic polymer has a solubility in water at 25° C. of more than 1% by weight, more than 5% by weight, or more than 10% by weight.

Exemplary hydrophilic polymers include, but are not limited to, chitosan, polyethylene-polypropylene glycol, poly(vinylalcohol) (PVA), carbomer, polycarbophil, hydrophilic polyurethanes, hydrophilic poly(meth)acrylates, polyvinylpyrrolidone, poly(carboxymethyl cellulose), poly[N-(2-hydroxypropyl)methacrylamide], combinations thereof, and others known to those skilled in the art.

In some embodiments of any one of the aspects described herein, the hydrophilic polymer is chitosan. For example, the polymer in the mixture with the active agent, e.g., the second polymer, is chitosan.

The amount of the hydrophilic polymer in the active agent mixture can range from about 0.1% to about 5% w/w or w/v of the mixture. For example, the amount of the hydrophilic polymer in the active agent mixture can range from about 0.2% to about 2.5%, from about 0.25% to about 2%, from about 0.50% to about 1.5%, or from about 0.75% to about 1.25% w/w or w/v of the mixture. Without wishing to be bound by a theory, the amount of the hydrophilic polymer in the active agent mixture can be adjusted as needed to obtain a desired rate of active agent release from the scaffold. The mechanism of release is by adsorption to the fibers and subsequent wetting of the mesh, dictated by the hydrophilic nature of the pores. Thus, when additional hydrophilic polymer, e.g., chitosan is added to the mixture comprising the active agent, release can be faster.

In some embodiments of any one of the aspects described herein, the polymer is an amphiphilic polymer. The term "amphiphilic polymer" means a polymer which comprises at least a hydrophilic part (the term "part" is also referred to hereinthroughout as "block", "domain" or "component", interchangeably) and at least a hydrophobic part. An amphiphilic polymer is water-soluble or water-dispersible, directly or e.g., by means of pre-dissolution in an organic solvent miscible with water. It is noted that the amphiphilic polymer can be a block copolymer or a graft copolymer.

The term "block copolymer" or "segmented copolymer" refers to a polymer comprising two or more chemically distinct regions or segments (referred to as "blocks") joined in a linear manner, that is, a polymer comprising chemically differentiated units that are joined (covalently bonded) end-to-end with respect to polymerized functionality (e.g., polymerized propylenic functionality), rather than in pendent or grafted fashion. Block copolymers comprise sequences ("blocks") of the same monomer unit, covalently bound to sequences of unlike type. The blocks can be connected in a variety of ways, such as A-B in diblock and A-B-A triblock structures, where A represents one block and B represents a different block. In a multi-block copolymer, A and B can be connected in a number of different ways and be repeated multiply. It may further comprise additional blocks of different type Multi-block copolymers may be linear multi-block, multi block star polymers (in which all blocks bond to the same atom or chemical moiety) or comb-like polymers where the B blocks are attached at one end to an A backbone. The block copolymers can be linear or branched. With respect to the block copolymers, the blocks may differ in the amount of comonomer incorporated therein. The blocks may also differ in the type of comonomer, density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property.

The term "graft copolymer" refers to a copolymer having a linear backbone of one polymer and randomly distributed side chains of another polymer.

Exemplary amphiphilic polymers include, but are not limited to, non-ionizable cellulosics such as hydroxypropyl methyl cellulose, hydroxyethyl methyl cellulose and hydroxyethyl cellulose acetate; non-acidic ionizable cellulosics such as amino ethyl cellulose acetate and hydroxybenzyl cellulose; and non-ionizable non-cellulosics such as polyvinylpyrrolidone, ethylene/vinyl alcohol copolymers and polyoxyethylene-polyoxypropylene block copolymers (also referred to as poloxamers); and ionizable non-cellulosics such as amine-functionalized polyacrylates and polymethacrylates, and combinations thereof. Exemplary diblock amphiphilic copolymers include, but are not limited to, polystyrene grafted with carboxyl-group-functionalized ethylene oxide (PS:PEG:COOH), polyethylene glycol)-block-polylactide (PEG-PLA), poly(ethylene glycol)-block-poly(lactide-co-glycolide)(PEG-PLGA), poly(ethylene glycol)-block-polyethylene (PEG-PE), and poly(ethylene glycol)-block-poly(e-caprolactone) (PEG-PCL)), and combinations thereof. Exemplary triblock amphiphilic copolymers include, but are not limited to, poly(ethylene glycol)-block-poly(propylene glycol)-block-poly(ethylene glycol) (PEG-PPG-PEG), and poly (propyl ene glycol)-block-poly (ethylene glycol-block-poly(propylene glycol) (PPG-PEG-PPG)), and combinations thereof.

In some embodiments of any one of the aspects described herein, the amphiphilic polymer is a polyoxyethylene polyoxypropylene block copolymer, e.g., a poloxamer (sold under the trade names SYNPERONICS™, PLURONIC™, and KOLLIPHOR™). In some embodiments of any one of the aspects described herein, the amphiphilic polymer is a poloxomer selected from the group consisting of poloxamer 407, sold under the tradename PLURONIC® F127), Poloxamer 188 (P188), poloxamer, sold under the tradename PLURONIC® F38, poloxamer, sold under the tradename PLURONIC® F68, poloxamer, sold under the tradename PLURONIC® F87, poloxamer, sold under the tradename PLURONIC® F108, poloxamer, sold under the tradename PLURONIC® 10R5, poloxamer, sold under the tradename PLURONIC® 17R2, poloxamer, sold under the tradename PLURONIC® 17R4, poloxamer, sold under the tradename PLURONIC® 25R2, poloxamer, sold under the tradename PLURONIC® 25R4, poloxamer, sold under the tradename PLURONIC® 31R1, poloxamer, sold under the tradename PLURONIC® F108 Cast Solid Surfacta, poloxamer, sold under the tradename PLURONIC® F108 NF, Pluronic® F108 Pastille, poloxamer, sold under the tradename PLURONIC® F108NF Prill Poloxamer 338, poloxamer, sold under the tradename PLURONIC® F127 NF, poloxamer, sold under the tradename PLURONIC® F127 NF 500 BHT Prill, poloxamer, sold under the tradename PLURONIC® F127 NF Prill Poloxamer 407, poloxamer, sold under the tradename PLURONIC® F38 Pastille, poloxamer, sold under the tradename PLURONIC® F68 LF Pastille, poloxamer, sold under the tradename PLURONIC® F68 NF, poloxamer, sold under the tradename PLURONIC® F68 NF Prill, poloxamer, sold under the tradename PLURONIC® F68 Pastille, poloxamer, sold under the tradename PLURONIC® F77, poloxamer, sold under the tradename PLURONIC® F77 Micropastille, poloxamer, sold under the tradename PLURONIC® F87 NF, poloxamer, sold under the tradename PLURONIC® F87 NF Prill Poloxamer 237, poloxamer, sold under the tradename PLURONIC® F 88, poloxamer, sold under the tradename PLURONIC® F 88 Pastille, poloxamer, sold under the tradename PLURONIC® F 98, poloxamer, sold under the tradename PLURONIC® FT L 61, poloxamer, sold under the tradename PLURONIC® L10, poloxamer, sold under the tradename PLURONIC® L101, poloxamer, sold under the tradename PLURONIC® L121, poloxamer, sold under the tradename PLURONIC® L31, poloxamer, sold under the tradename PLURONIC® L35, poloxamer, sold under the tradename PLURONIC® L43, poloxamer, sold under the tradename PLURONIC® L61, poloxamer, sold under the tradename PLURONIC® L62, poloxamer, sold under the tradename PLURONIC® L62 LF, poloxamer, sold under the tradename PLURONIC® L62D, poloxamer, sold under the tradename PLURONIC® L64, poloxamer, sold under the tradename PLURONIC® L81, poloxamer, sold under the tradename PLURONIC® L92, poloxamer, sold under the tradename PLURONIC® L44 NF INH surfactant Poloxamer 124, poloxamer, sold under the tradename PLURONIC® N3, poloxamer, sold under the tradename PLURONIC® P103, poloxamer, sold under the tradename PLURONIC® P104, poloxamer, sold under the tradename PLURONIC® P105, poloxamer, sold under the tradename PLURONIC® P123 Surfactant, poloxamer, sold under the tradename PLURONIC® P65, poloxamer, sold under the tradename PLURONIC® P84, poloxamer, sold under the tradename PLURONIC® P85, and the like.

In some embodiments of any one of the aspects described herein, the hydrophilic polymer is chitosan. For example, the polymer in the mixture with the second polymer and the active agent, e.g., the third polymer is a poloxamer, e.g., poloxamer 407, sold under the tradename PLURONIC® F127).

Without addition of the third polymer, i.e., an amphiphilic polymer poor wetting can lead to failure of the active agent comprising mixture to incorporate within the pores of the scaffold. This can lead to rapid release of the active agent and release can occur in a week or less. Thus, inclusion of the third polymer, i.e., an amphiphilic polymer into the mixture comprising the active agent can enhance or increase incorporation of the active agent mixture within the pores of the scaffold.

The amount of the amphiphilic polymer in the mixture comprising the active agent can be adjusted as needed. For example, the amount of the amphiphilic polymer in the mixture comprising the active agent can be from 0.01% to about 1% w/w or w/v of the mixture. In some embodiments of any one of the aspects described herein, the amount of the amphiphilic polymer in the mixture comprising the active agent is from about 0.02% to about 0.75%, from about 0.03% to about 0.5%, from about 0.04% to about 0.25%, from about 0.05% to about 0.2%, from about 0.06% to about 0.175%, from about 0.07% to about 0.15% or from about 0.075% to about 0.125% w/w or w/v of the mixture. In some embodiments of any one of the aspects described herein, the amount of the amphiphilic polymer in the mixture comprising the active agent is about 0.1% w/w/or w/v of the mixture comprising the active agent.

In some embodiments of any one of the aspects described herein, the polymer is polyamidosaccharide. For example, the polymer in particle comprising the active agent and the second polymer the mixture with the active agent, e.g., the fourth polymer, is polyamidosaccharide (PAS).

In some embodiments of any one of the aspects described herein, the active agent and the fourth polymer self-assemble into particles when combined together.

A polymer useful in the drug delivery compositions described herein can be a bio-compatible polymer. As used herein, the term "biocompatible" refers to a material's ability to perform its intended function, with a desired degree of incorporation in the host, without eliciting any undesirable local or systemic effects in that host. As used herein, the term "biocompatible" means exhibition of essentially no cytotoxicity or immunogenicity while in contact with body fluids or tissues. The term "biocompatible polymer" refers to polymers which are non-toxic, chemically inert, and substantially non-immunogenic/non-inflammatory while in contact with body fluids or tissues.

In some embodiments of any one of the aspects described herein, the polymer of the scaffold, e.g., the first polymer is a bio-compatible polymer.

In some embodiments of any one of the aspects described herein, the second polymer is a bio-compatible polymer.

In some embodiments of any one of the aspects described herein, the third polymer is a bio-compatible polymer.

In some embodiments of any one of the aspects described herein, the fourth polymer is a bio-compatible polymer.

A polymer useful in the drug delivery compositions described herein can be a biodegradable polymer. Biodegradable polymers are disclosed in the art. Examples of suitable biodegradable polymers include, but are not limited to, linear-chain polymers such as polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), and copolymers, terpolymers, and copolymers including one or more of the foregoing. Other biodegradable polymers include, for example, gelatin, collagen, silk, chitosan, alginate, cellulose, poly-nucleic acids, etc. In some embodiments of any one of the aspects described herein, the polymer of the scaffold, e.g., the first polymer is a biodegradable polymer.

In some embodiments of any one of the aspects described herein, the second polymer is a biodegradable polymer.

In some embodiments of any one of the aspects described herein, the third polymer is a biodegradable polymer.

In some embodiments of any one of the aspects described herein, the fourth polymer is a biodegradable polymer.

Embodiments of the various aspects described herein include an active agent. An "active agent" is any compound or substance that has some desired activity. Exemplary types of active agents include, but are not limited to, small organic or inorganic molecules, amino acids, peptides, polypeptides, nucleoproteins, mucoproteins, lipoproteins, glycoproteins, nucleosides and nucleotides, oligonucleotides, polynucleotides, carbohydrates, monosaccharides, oligosaccharides, polysaccharides, lipids, hormones, steroids, vitamins, receptor ligands, cells, and extract made from a biological material.

In some embodiments of any one of the aspects described herein, the active agent is a therapeutic agent. A "therapeutic agent" is a molecule, composition or other substance that provides a therapeutic effect. Therapeutic agent includes any natural or synthetic molecule or substance intended to provide benefit to the subject administered the molecule or substance, including the treatment of a disease. Generally, a therapeutic agent is a pharmaceutically active compound. Exemplary pharmaceutically active compound include, but are not limited to, those found in Harrison's Principles of Internal Medicine, 13th Edition, Eds. T. R. Harrison McGraw-Hill N.Y., NY; Physicians Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index. Some exemplary therapeutic agents include, but are not limited to, antiplatelets, antithrombins, anti-adhesion agents, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, protein receptor agonists or antagonists, anti-stenosis agents, isolates, enzymes, monoclonal antibodies, ribonucleases, nutraceutical agents (e.g. vitamins, minerals, etc.), labeling agents (e.g., contrast agents, radionuclides, fluorescent agents, luminescent agents, magnetic agents), and any combinations thereof.

In some embodiments of any one of the aspects described herein, the active agent is an anti-cancer agent. Exemplary anti-cancer agents include, but are not limited to, mitogen-activated protein kinase kinase (MEK) (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostin; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3;

interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. TAXOL™ (i.e. paclitaxel), TAXOTERE™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™) erlotinib (TARCEVA™), cetuximab (ERBITUX™), lapatinib (TYKERB™), panitumumab (VECTIBX™) vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or analogues or derivatives thereof.

In some embodiments of the various aspects described herein, the active agent is an anti-inflammatory agent. As used herein the term "anti-inflammatory agent" refers to a compound (including its analogs, derivatives, prodrugs and pharmaceutically salts) which can be used to treat inflammation or an inflammation related disease or disorder. Exemplary anti-inflammatory agents include, but are not limited to, the known steroidal anti-inflammatory and non-steroidal anti-inflammatory drugs (NSAIDs). Exemplary steroidal anti-inflammatory agents include but are not limited to 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethyl-amino-acetate, prednisolone sodium phosphate, prednisone, prednival, prednylidene, rimexolone, tixocortol, triamcinolone, triamcinolone acetonide, triamcinolone benetonide, triamcinolone hexacetonide, and analogues and derivatives thereof. Exemplary nonsteroidal anti-inflammatory agents include but are not limited to COX inhibitors (COX-1 or COX nonspecific inhibitors) and selective COX-2 inhibitors. Exemplary COX inhibitors include but are not limited to salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; and analogues and derivatives thereof. Exemplary COX-2 inhibitors include but are not limited to diarylsubstituted furanones such as refecoxib; diaryl-substituted pyrazoles such as celecoxib; indole acetic acids such as etodolac and sulfonanilides such as nimesulide; and analogues and derivatives thereof.

In some embodiments of the various aspects described herein, the active agent is an antibiotic. Exemplary antibiotics include, but are not limited to, antibacterial agents, antifungal agents, and antiviral agents.

In some embodiments of the various aspects described herein, the active agent is an antibacterial agent. As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria. Examples of antibacterial agents include, but are not limited to, macrolides or ketolides such as erythromycin, azithromycin, clarithromycin, and telithromycin; beta-lactams including penicillin, cephalosporin, and carbapenems such as carbapenem, imipenem, and meropenem; monolactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, cefriaxone, cefoperazone, ceftazidime, cefixime, cefpodoxime, ceftibuten, cefdinir, cefpirome, cefepime, and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomvcin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; trimethoprim, bacitracin, and phosphonomycin.

In some embodiments of the various aspects described herein, the active agent is an antifungal agent. As used herein, the term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus. Examples of antifungal agents include, but are not limited to, azoles (e.g., barleyconazole, butoconazole, clortrimazole, econazole, fluconazole, isavuconazole, itraconazole, ketoconazole, miconazole, oxyconazole, posaconazole, ravuconazole, saperconazole, sulconazole, tercocnazole, tioconazole, voriconazole, and ciclopirox), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone, fenpropimorph, terbinafine, cyclopyroxolamine, flucitocin, griseofulvin haloprozin, tolnaftate, naphthypine, hydrochloride, morpholine, butenapin, undecylenic acid, propionic acid, and derivatives and analogs thereof.

In some embodiments of the various aspects described herein, the active agent is an antiviral agent. Exemplary antiviral agents include, but are not limited to polymerase inhibitors, viral entry inhibitors, viral maturation inhibitors, capsid assembly modulators, IMPDH inhibitors, protease inhibitors, immune-based therapeutic agents, reverse transcriptase inhibitors, and TLR-agonists. Some specific exemplary antiviral agents include, but are not limited to, acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, interferons, and analogues and derivatives thereof.

In some embodiments of any one of the aspects described herein, the active agent is a wound repairing or healing agent. As used herein, the term "wound healing agent" refers to any synthetic or natural, biological or chemical agent, which promotes the healing of acute or chronic wounds and/or prevents or lessens the formation of scar tissue. Exemplary wound healing agents include, but are not limited to, dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols;

nitrates and anthocyanins; nucleosides, such as adenosine; and nucleotides, such as adenosine diphosphate (ADP) and adenosine triphosphate (ATP); neurotransmitter/neuromodulators, such as acetylcholine and 5-hydroxytryptamine (serotonin/5-HT); histamine and catecholamines, such as adrenalin and noradrenalin; lipid molecules, such as sphingosine-I-phosphate and lysophosphatidic acid; amino acids, such as arginine and lysine; peptides such as the bradykinins, substance P and calcium gene-related peptide (CGRP); nitric oxide; and any combinations thereof. Exemplary growth factors include, but are not limited to, fibroblast growth factor (FGF), FGF-1, FGF-2, FGF-4, FGF-a, FGF-P, plateletderived growth factor (PDGF), insulin binding growth factor (IGF), IGF-1, IGF-2, heparin-binding growth factor-1, heparin-binding growth factor-2, epidermal growth factor (EGF), transforming growth factor (TGF), TGF-a, TGF-P, cartilage inducing factors-A and -B, osteoid-inducing factors, osteogenin, vascular endothelial growth factor, bone growth factors, collagen growth factors, insulin-like growth factors, and their biologically active derivatives.

In some embodiments of any one of the aspects described herein, the active agent is an antiplatelet. Exemplary antiplatelets include, but are not limited to, irreversible cyclooxygenase inhibitors, Aspirin, Adenosine diphosphate (ADP) receptor inhibitors, Clopidogrel (Plavix), Prasugrel (Effient), Ticagrelor (Brilinta), Elinogrel, Ticlopidine (Ticlid), Phosphodiesterase inhibitors, Cilostazol (Pletal), Glycoprotein IIB/IIIA inhibitors (intravenous use only), Abciximab (ReoPro), Eptifibatide (Integrilin), Tirofiban (Aggrastat), Adenosine reuptake inhibitors, PAR-1 or PAR-4 antagonists, GPVI antagonists, Dipyridamole (Persantine), Thromboxane inhibitors, Thromboxane synthase inhibitors, Thromboxane receptor antagonists, Terutroban, and mixtures thereof.

In some embodiments of any one of the aspects described herein, the active agent is an antithrombin. Exemplary antithrombins include, but are not limited to, heparin, aspirin, hirudin, dabigatran, Enoxaparin, anti-Xa, anti-XIIa, anti-IXa agents, GPIIb/IIIa receptor inhibitor as tirofiban, eptifibatide, cilostazol, plavix, Ticlid, urokinase, and PPack (dextrophenylalanine proline arginine chloromethylketone. Suitable anti-cancer agents include methotrexate, purine, pyridine, and botanical (e.g. paclitaxel, colchicines and triptolide), epothilone, antibiotics, and antibodies.

In some embodiments of any one of the aspects described herein, the active agent is an anti-adhesion agent. Exemplary anti-adhesion agents include, but are not limited to, any agent that blocks and/or inhibits an adhesion molecule such as, e.g., cell adhesion molecules (CAM), intercellular adhesion molecules (ICAM), vascular cell adhesion molecules (VCAM), and others. Agents that block such adhesion molecules can include, e.g., antibodies, RNAi agents. Exemplary anti-adhesion agents include, by way of example only, ocriplasmin.

In some embodiments of any one of the aspects described herein, the active agent is a vasoconstrictor. As used herein, the term "vasoconstrictor" refers to compounds or molecules that narrow blood vessels and thereby maintain or increase blood pressure, and/or decrease blood flow. There are many disorders that can benefit from treatment using a vasoconstrictor. For example, redness of the skin (e.g., erythema or cuperose), which typically involves dilated blood vessels, benefit from treatment with a vasoconstrictor, which shrinks the capillaries thereby decreasing the untoward redness. Other descriptive names of the vasoconstrictor group include vasoactive agonists, vasopressor agents and vasoconstrictor drugs. Certain vasoconstrictors act on specific receptors, such as vasopressin receptors or adrenoreceptors. Exemplary vasoconstrictors include, but are not limited to, alpha-adrenoreceptor agonists, chatecolamines, vasopressin, vasopressin receptor modualors, calcium channel agonists, and other endogenous or exogenous vasoconstrictors.

In some embodiments, the vasoconstrictor is selected from the group consisting of aluminum sulfate, amidephrine, amphetamines, angiotensin, antihistamines, argipressin, bismuth subgallate, cafaminol, caffeine, catecholamines, cyclopentamine, deoxyepinephrine, dopamine, ephedrine, epinephrine, felypressin, indanazoline, isoproterenol, lisergic acid diethylamine, lypressin (LVP), lysergic acid, mephedrone, methoxamine, methylphenidate, metizoline, metraminol, midodrine, naphazoline, nordefrin, norepinephrine, octodrine, ornipressin, oxymethazoline, phenylefhanolamine, phenylephrine, phenylisopropylamines, phenylpropanolamine, phenypressin, propylhexedrine, pseudoephedrine, psilocybin, tetrahydralazine, tetrahydrozoline, tetrahydrozoline hydrochloride, tetrahydrozoline hydrochloride with zinc sulfate, tramazoline, tuaminoheptane, tymazoline, vasopressin, vasotocin, xylometazoline, zinc oxide, and the like In some embodiments of any one of the aspects described herein, the active agent is a vasodilator. A vasodilator can be selected from the group consisting of alpha-adrenoceptor antagonists (alpha-blockers), agiotensin converting enzyme (ACE) inhibitors, angiotensin receptor blockers (ARBs), beta2-adrenoceptor agonists (β2-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, renin inhibitors, and any combinations thereof. Exemplary vasodilator include, but are not limited to, prazosin, terazosin, doxazosin, trimazosin, phentolamine, phenoxybenzamine, benazepril, captopril, enalapril, fosinopril, lisinopril, moexipril, quinapril, ramipril, candesartan, eprosartan, irbesartan, losartan, olmesartan, telmisartan, valsartan, Epinephrine, Norepinephrine, Dopamine, Dobutamine, Isoproterenol, amlodipine, felodipine, isradipine, nicardipine, nifedipine, nimodipine, nitrendipine, clonidine, guanabenz, guanfacine, α-methyldopa, hydralazine, Bosentan, trimethaphan camsylate, isosorbide dinitrate, isosorbide mononitrate, nitroglycerin, erythrityl tetranitrate, pentaerythritol tetranitrate, sodium nitroprusside, milrinone, inamrinone (formerly amrinone), cilostazol, sildenafil, tadalafil, minoxidil, aliskiren, and analogs, derivatives, prodrugs, and pharmaceutically acceptable salts thereof.

In some embodiments of any one of the aspects described herein, the active agent is an immunosuppressive agent. Exemplary immunosuppressive agents include, but are not limited to, Azathioprine, cyclosporine, interferon, opioids, TNF-binding proteins, infliximab (Remicade), etanercept (Enbrel), or adalimumab, Mycophenolic acid, Fingolimod, Myriocin.

In some embodiments of any one of the aspects described herein, the active agent is an anti-infective agent. Exemplary anti-infective agents include, but are not limited to, pyrimidine analogs, chlorhexidine, silver compounds (e.g., silver chloride, silver nitrate, silver oxide), silver ions, silver particles, gold compounds (such as gold chloride, auranofin), gold ions, gold particles, iodine, povidone/rodine, chlorhexidine, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefinenoxime, cefininox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, azaserine, candicidin(s), chlorphenesin, dermostatin(s), filipin, fungichromin, mepartricin, nystatin, oligomycin(s), ciproflaxacin, norfloxacin, ofloxacin, pefloxacin, enoxacin, rosoxacin, amifloxacin, fleroxacin, temafloaxcin, lomefloxacin, perimycin A or tubercidin, and the like.

In some embodiments of any one of the aspects described herein, the active agent is an anti-proliferative agent. Exemplary anti-proliferative (e.g., anti-neoplastic) agents include, but are not limited to, tubulin interacting agents, topoisomerase inhibitors and agents, acitretin, alstonine, amonafide, amphethinile, amsacrine, ankinomycin, anti-neoplaston, aphidicolin glycinate, asparaginase, angiopeptin, acetylsalicylic acid, baccharin, batracylin, benfluoron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, enoxaprin, epothilones, ergotamine, etoposide, etretinate, fenretinide, gallium nitrate, genkwadaphnin, hexadecylphosphocholine, hirudin, histone deacetylase (HDAC) inhibitors, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylateddehydroalanines, nafazatrom, nocodazole derivative, octreotide, oquizanocine, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, withanolides, and monoclonal antibodies capable of blocking smooth muscle cell proliferation.

In some embodiments of any one of the aspects described herein, the active agent is an antimetabolite agent. Exemplary antimetabolite agents include but are not limited to, 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, inhibitors of essential amino acids, isopropyl pyrrolizine, methobenzaprim, methotrexate, norspermidine, ornithine decarboxylantion inhibitors, pentostatin, piritrexim, plicamycin, thioguanine, tiazofurin, trimetrexate, tyrosine kinase inhibitors, and uricytin.

In some embodiments of any one of the aspects described herein, the active agent is an alkylating agent. Exemplary alkylating agents include, e.g., aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol.

In some embodiments of any one of the aspects described herein, the active agent is an anesthetic agent. Exemplary anesthetic agents include, but are not limited to, procaine, amethocaine, cocaine, lidocaine (also known as Lignocaine), prilocaine, bupivacaine, levobupivacaine, ropivacaine, mepivacaine, dibucaine, Barbiturates, Amobarbital, Methohexital, Thiamylal, Thiopental, Benzodiazepines, Diazepam, Lorazepam, Midazolam, Etomidate, Ketamine, Propofol, Alfentanil, Fentanyl, Remifentanil, Sufentanil, Buprenorphine, Butorphanol, diacetyl morphine, Hydromorphone, Levorphanol, Meperidine, Methadone, Morphine, Nalbuphine, Oxycodone, Oxymorphone, Pentazocine, and mixtures thereof.

In some embodiment of any one of the aspects described herein, the active agent is an anti-viral agent. Exemplary anti-viral agents include, but are not limited to, aciclovir, amantadine, antiviral proteins, alovudine, arbidol, brivudine, 5-bromouridine, cidofovir, daclatasvir, template: DNA antivirals, docosanol, double-stranded RNA (ds RNA) activated caspase oligomerizer (DRACO), famciclovir, FGI-104, fialuridine, fomivirsen, foscarnet, FV-100, ganciclovir, ibacitabine, idoxuridine, imiquimod, inosine, inosine pranobex, interferon, interferon alfa-2b, interferon alfacon-1, interferon alpha-n3, interferon type I, interferon type IL, interferon type III, interferon-gamma, maribavir, methisazone, moroxydine, nucleoside analogue, oragen, peginterferon alfa-2a, pegylated interferon, penciclovir, pleconaril, podophyllotoxin, prosetta, PSI-6130, reciGen, resiquimod, ribavirin, rintatolimod, template: RNA antivirals, semapimod, setrobuvir, simeprevir, sofosbuvir, sorivudine, tecovirimat, taribavirin, telbivudine, tenofovir alafenamide fumarate, theaflavin, tilorone, trifluridine, tromantadine, valaciclovir, valganciclovir and vidarabine.

In some embodiments of any one of the aspects described herein, the active agent is an antiseptic. Exemplary antiseptics include, but are not limited to, alcohols (like ethanol, 1-propanol, 2-propanol), quaternary ammonium salts also known as quats or QAC's (For example benzalkonium chloride (BAC), cetyl trimethylammonium bromide (CTMB), cetylpyridinium chloride (Cetrim, CPC) and benzethonium chloride (BZT)), boric acid, brilliant green, chlorhexidine gluconate, hydrogen peroxide, iodine (for example providone-iodine and Lugol's iodine), mercurochrome, manuka money, octenidine dihydrochloride, phenol (carbolic acid) compounds, polyhexanide (polyhexamethylene biguanide, PHMB), sodium chloride, sodium hyposhlorite, calcium hypochlorite and sodium bicarbonate.

In some embodiments of any one of the aspects described herein, the active agent is an antibody. For example, the active agent is a monoclonal antibody. Non-limiting examples of monoclonal antibodies include rituximab, trastuzumab, gemtuzumab, ozogamicin, alemtuzumab, ibritumomab, tiuxetan, tositumomab, cetuximab, bevacizumab, panitumumab, and ofatumumab. In some embodiments of any one of the aspects described herein, the active agent is a human or humanized antibody.

In some embodiments of the various aspects described herein, the active agent is an imaging agent. As used herein, the term "imaging agent" refers to an element or functional group in a molecule capable of producing a detectable signal. The imaging agent can be an optical reporter, non-metallic isotope, a boron neutron absorber, a paramagnetic metal ion, a ferromagnetic metal, a gamma-emitting radioisotope, a positron-emitting radioisotope, or an x-ray absorber. Optical properties that can be detected include, but are not limited to, fluorescence, absorbance, reflectance, birefringence, optical scattering and the like.

The active agent is incorporated into the scaffold by zipFv, spontaneously forming nanoparticles with polyamidosaccharide (PAS), which stabilizes the protein through the mesh fabrication process. The nanoparticles are dispersed in a 1% chitosan solution, which is dropcast onto a polycaprolactone (PCL) electrospun nanofiber mesh similar to many surgical meshes in use today. The chitosan and zipFv-nanoparticles fill the pores of the mesh and are released slowly over time in physiologic conditions.

In some embodiments of any one of the aspects described herein, the active agent can be conjugated with a ligand. For example, the active agent can be conjugated with a targeting ligand. As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

In some embodiments of any one of the aspects described herein, the targeting ligand is a first member of a binding pair. As used herein, the term "binding pair" refers to a pair of moieties that specifically bind each other with high affinity, generally in the low micromolar to picomolar range. When one member of a binding pair is conjugated to a first element and the other member of the pair is conjugated to a second element, the first and second elements will be brought together by the interaction of the members of the binding pair. Non-limiting examples of binding pairs include antigen:antibody (including antigen-binding fragments or derivatives thereof), biotin:avidin, biotin:streptavidin, biotin:neutravidin (or other variants of avidin that bind biotin such as), receptor:ligand, and the like. Additional molecule for binding pair can include, neutravidin, strep-tag, streptactin and derivatives, and other peptide, hapten, dye-based tags-anti-Tag combinations such as SpyCatcher-SpyTag, His-Tag, Fc Tag, Digitonin, GFP, FAM, haptens, SNAP-TAG. HRP, FLAG, HA, myc, glutathione S-transferase (GST), maltose binding protein (MBP), small molecules, and the like. Some exemplary pair of molecules include, but are not limited to, a receptor and ligand, nucleic acid and nucleic acid binding protein, antibody and antigen, antigen binding fragment of an antibody and antigen, antibody and Fc receptor, antibody and protein A, aptamer and its binding target, a drug and its target, and the like.

In some embodiments of any one of the aspects described herein, the binding pair is a pair of protein interaction domains. As used herein, "protein interaction domain" refers to a domain that permits specific binding of two separate polypeptides to each other Exemplary protein interaction domains are known in the art and can be used in embodiments of the aspects described herein. In some embodiments of any one of the aspects described herein, the protein interaction domains are leucine zipper domains. In some embodiments of any of the aspects, the protein interaction domains are PSD95-D1g1-zo-1 (PDZ) domains. In some embodiments of any of the aspects, one protein interaction domain is streptavidin and a second protein interaction domain is streptavidin binding protein (SBP). In some embodiments of any of the aspect, one protein interaction domain is FKBP-binding domain of mTOR (FRB) and a second protein interaction domain is FK506 binding protein (FKBP); one protein interaction domain is cyclophilin-Fas fusion protein (CyP-Fas) and a second protein interaction domain is FK506 binding protein (FKBP); one protein interaction domain is calcineurinA (CNA) and a second protein interaction domain is FK506 binding protein (FKBP), one protein interaction domain is gibberellin insensitive (GIA) and a second protein interaction domain is gibberellin insensitive dwarf1 (GID1); one protein interaction domain is Snap-tag and a second protein interaction domain is Halo tag; or one protein interaction domain is T14-3-3-cdeltaC and a second protein interaction domain is C-Terminal peptides of PMA2 (CT52).

In some embodiments of any one of the aspects described herein, the protein interaction domains are leucine zipper domains. Leucine zipper domains are a type of protein-protein interaction domain commonly found in transcription factors characterized by leucine residues evenly spaced through an a-helix. Leucine zippers may form heterodimers or homodimers. A number of leucine zipper domains, as well as their ability to bind each other, are known in the art and discussed further, e.g., in Reinke et al. JACS 2010 132: 6025-31 and Thomposon et al. ACS Synth Biol 2012 1: 118-129; each of which is incorporated by reference herein in its entirety. In some embodiments of any of the aspects, one leucine zipper domain is BZip (RR) and the second leucine zipper domain is AZip (EE).

In some embodiments of any one of the aspects described herein, the active agent is a chimeric antigen receptor. For example, the active agent is a multi-component chimeric antigen receptor described in US patent publication US20180346541, content of which is incorporated herein by reference in its entirety. Generally, a multi-component chimeric antigen receptor comprises: (a) a target binding domain (e.g., an antibody reagent specific for a first target ligand) and a first interaction domain (e.g., a protein interaction domain); and (b) a first signaling domain capable of binding specifically with the first interaction domain (e.g., a signaling polypeptide comprising an extracellular protein interaction domain that can bind specifically with the protein interaction domain), and a second signaling domain (e.g., an intracellular T cell receptor (TCR) signaling domain).

In some embodiments of any one of the aspects described herein, the drug delivery composition is in form of an implantable device. As used herein, the term "implantable" refers to the attribute of being implantable in subject, e.g. a mammal such as a human. As used herein, the term "implantable device" means that the device is suitable for use in vivo, i.e., by implantation into a subject, e.g., a mammal such as human. As used herein, the term "implantable device" is used interchangeably with the term "medical device."

In some embodiments of any one of the aspects described herein, the drug delivery composition is in form of a drug depot.

In some embodiments of any one of the aspects described herein, the drug delivery composition can be coated on a surface of an implantable device. Examples of implantable devices include, but are not limited to, wound caring articles, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, artificial heart valves, anastomotic clips, arterial closure devices, patent foramen ovale closure devices, and cerebrospinal fluid shunts.

In some embodiments of any one of the aspects described herein, the drug delivery composition can comprise additional components. For example, the drug delivery composition can be a pharmaceutical composition further comprising a pharmaceutically acceptable carrier or excipient.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The drug delivery compositions described herein can be used for can be used to deliver an active agent to the cell. Accordingly, in another aspect provided herein is a method for delivering an active agent to a cell. Generally, the method comprises contacting a cell with a drug delivery composition described herein. Methods for contacting to a cell are well known and available to one of skill in the art. Generally, the cell can be contacted with the drug delivery composition in a cell culture e.g., in vitro or ex vivo, or the drug delivery composition can be administered to a subject, e.g., in vivo. The term "contacting" or "contact" as used herein in connection with contacting a cell includes subjecting the cells to an appropriate culture media, which comprises a drug delivery composition described herein. Where the cell is in vivo, "contacting" or "contact" includes administering the drug delivery composition to a subject via an appropriate administration route.

The drug delivery compositions provided herein can be utilized to promote healing or prevent disease by targeting pophylactic or therapeutic drug to a local and/or regional areas. Accordingly, in another aspect, the disclosure provides methods of treatment of diseases and disorders comprising the step of delivering a drug delivery composition described herein to a specific cell or tissue location wherein a therapeutic agent is desired to be delivered. The delivery site of interest can include the following: specific cell types, a tissue, an organ, a wound, a lymph node, an established tumor, the remains of a tumor from a surgically resected tumor, etc. It can also be sites of inflammation or specific organs or biologic locations or sites of pathologic processes such as inflammation, such as in joints, where increased local drug concentrations are desired. Such a drug delivery system reduces systemic exposure of an agent and increases the local concentration of an agent at the tissue site.

In some embodiments, the drug delivery composition is administered on the surface of cancerous tissue or the site remaining after surgical resection and releases one or more anticancer agents in a gradual and prolonged manner to reduce or kill tumors and/or prevent recurrence or metastasis in tissues including but not limited to lung, colon, ovary, breast, pancreas, mesothelium, connective tissue, stomach, liver, and kidney. As such these drug delivery compositions are of use for treating sarcomas, mesothelioma, lung cancer, breast cancer, colon cancer, ovarian cancer, etc. In some embodiments, the drug delivery composition is administered to the resection margins after local surgery following the removal of a tumor to destroy residual remaining disease and prevent recurrence. The composition can be loaded with one or more prohealing drugs such as anti-inflammatories in addition to anticancer agents to ensure adequate healing of noncancerous tissue. In some embodiments, the composition is implanted e.g., stapled directly over the surface of diseased or treated tissue. The implants can also be combined with other therapeutic modalities, including radiotherapy, other chemotherapeutic agents administered systemically or locally, immunotherapy, or radiofrequency ablation. In some embodiments, the implant is administered to the site of disease utilizing methods currently used during standard surgical resection procedures, for example by simultaneously administering the composite using the surgical stapler during the removal of the primary tumor. By the appropriate selection of polymers, and active agent, a flexible implant capable of controlled release of a therapeutic agent to the surface of a tissue can be constructed.

In some embodiments of various aspects described herein, the drug delivery compositions described herein can be used for wound management, e.g., but not limited to, sealing, treating, and/or repairing wounds, treatment of burns or other traumatized or degenerative tissue, or repair or replacement of tissues or organs. For example, a method for wound management comprises contacting a wound in a subject with a drug delivery composition described herein.

In some embodiments of any one of the aspects described herein, the method comprises applying a drug delivery composition described herein one or more of the following: (i) a surgical resection margin, (ii) within a treated or untreated tumor or cavity, (iii) a target site of disease away from a surgical margin, (iv) a lymph node, and (v) a wound.

In some embodiments, the scaffold can be used with cell culture or co-culture. In some embodiments, the scaffold can be used with organ(s) or organoid tissue. Exemplary examples of cell culture or co-culture include, but are not limited to jurkat T cells, NALM6 cells transduced with HER2, primary CD4+ cells, and primary CD8+ cells, primary CD8+ HER2-targeted NS3 CAR T cells. Exemplary examples of organ(s) or organoid tissue includes, but is not limited to, such as intestine, stomach, heart, kidney, bladder, pancreas, liver, lung, brain, skin, and uterus.

Some exemplary embodiments of the various aspects described herein can be any one of the following numbered embodiments:

Embodiment 1: A drug delivery composition comprising: (a) a scaffold comprising electrospun nanofibers of a first polymer and wherein the scaffold comprises a plurality of pores; and (b) an active agent, and wherein: (i) the active agent is present in a mixture comprising the active agent, a second polymer and a third polymer, and wherein the mixture is present in the pores of the scaffold; or (ii) the active agent is distributed inside the nanofibers or adsorbed on the nanofibers, and wherein the first polymer is hydrophobic, wherein the second polymer is hydrophilic, and wherein the third polymer is an amphiphilic polymer.

Embodiment 2: The drug delivery composition of Embodiment 1, wherein the active agent is present in a mixture comprising the active agent and a second polymer and a third polymer.

Embodiment 3: The drug delivery composition of Embodiment 1 or 2, wherein the active agent is comprised in a particle, e.g., a nanoparticle.

Embodiment 4: The drug delivery composition of Embodiment 3, wherein the particle comprises a fourth polymer and wherein the fourth polymer is different from the first, second or third polymer.

Embodiment 5: The drug delivery composition of Embodiment 4, wherein the second and fourth polymer are different.

Embodiment 6: The drug delivery composition of Embodiment 4 or 5, wherein the fourth polymer and the active agent self-assemble to form the nanoparticle.

Embodiment 7: The drug delivery composition of any one of Embodiments 4-6, wherein the fourth polymer is a polyamidosaccharide.

Embodiment 8: The drug delivery composition of any one of Embodiments 1-7, wherein the third polymer is a poloxamer.

Embodiment 9: The drug delivery composition of any one of Embodiments 1-8, wherein the second polymer is chitosan. The drug delivery composition of any one of Embodiments 1-9, wherein the active agent is hydrophilic.

Embodiment 10: The drug delivery composition of Embodiment 1, wherein the active agent is distributed inside the nanofibers or adsorbed on the nanofibers.

Embodiment 11: The drug delivery composition of Embodiment 10, wherein the active agent is hydrophobic.

Embodiment 12: The drug delivery composition of any one of Embodiments 10-11, wherein the nanofibers have a diameter from about 50 nm to about 175 nm, e.g., a diameter from about 75 nm to about 125 nm.

Embodiment 13: The drug delivery composition of any one of Embodiments 1-12, wherein the first polymer is polycaprolactone (PCL).

Embodiment 14: The drug delivery composition of any one of Embodiments 1-13, wherein the active agent is a small organic or inorganic molecule, peptide, polypeptide, oligonucleotide, polynucleotide, oligosaccharide, or polysaccharide, an extract made from a biological material.

Embodiment 15: The drug delivery composition of any one of Embodiments 1-14, wherein the active agent is conjugated with a targeting ligand.

Embodiment 16: The drug delivery composition of Embodiment 16, wherein the targeting ligand is a first member of a binding pair.

Embodiment 17: The drug delivery composition of Embodiment 17, wherein the binding pair is a pair of protein interaction domains.

Embodiment 18: The drug delivery composition of Embodiment 18, wherein protein interaction domains are leucine zipper domains.

Embodiment 19: The drug delivery composition of any one of Embodiments 1-18, wherein the active agent is an antibody or an antigen binding fragment thereof.

Embodiment 20: The drug delivery composition of any one of Embodiments 1-19, wherein the active agent is zipFV.

Embodiment 21: The drug delivery composition of any one of Embodiments 1-, wherein the active agent is selected from the group consisting of anti-cancer agents, anti-inflammatory agents, antibiotic agents or antibacterial agents, anti-proliferatives, anti-migratory agents, anti-fibrotic agents, proapoptotics, anti-neoplastics, and immuno-suppressants.

Embodiment 22: The drug delivery composition of Embodiment 1, wherein the active agent is present in a mixture comprising the active agent and a second polymer and a third polymer, and wherein: (a) the first polymer is polycaprolactone; (b) the second polymer is chitosan; and (c) the third polymer is poloxamer 407, sold under the tradename Pluronic® F-127.

Embodiment 23: The drug delivery composition of Embodiment 23, wherein the active agent is comprised in a nanoparticle, and where the nanoparticle further comprises a polyamidosaccharide.

Embodiment 24: The drug delivery composition of Embodiment 23 or 24, wherein the active agent is zipFV.

Embodiment 25: The drug delivery composition of any one of Embodiments 1-25, wherein the drug delivery composition provides sustained release of the active agent.

Embodiment 26: The drug delivery composition of Embodiment 26, wherein sustained release of the active agent occurs for a period of at least ten days, e.g. at least 10 days, at least 25 days, at least 50 days, at least 90 days or more.

Embodiment 27: The drug delivery composition of any one of Embodiments 1-26, wherein the scaffold is a nonwoven mesh.

Embodiment 28: The drug delivery composition of any one of Embodiments 1-27, wherein the drug delivery composition is in form of an implantable device.

Embodiment 29: A pharmaceutical composition comprising the drug delivery composition of any one of Embodiments 1-28 and a pharmaceutically acceptable carrier or excipient.

Embodiment 30: A method of delivering an active agent to a cell, the method comprising contacting a cell with the drug delivery composition of any one of Embodiments 1-28.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "significantly different than,", "statistically significant," and similar phrases refer to comparisons between data or other measurements, wherein the differences between two compared data or other measurements are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The term "a reference level" as used herein refer to a negative control. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level used herein refers to the level measured prior to onset of treatment.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively, or additionally, the treatment can be administered after initiation of the disease or condition, for a therapeutic action.

In some embodiments, treatment is therapeutic and does not include prophylactic treatment.

As used herein, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult, child and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc.

In some embodiments, the subject is a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of a fibrotic disease or disorder.

It is noted that a human subject can be of any age, gender, race or ethnic group, e.g., Caucasian (white), Asian, African, black, African American, African European, Hispanic, Middle eastern, etc.

In addition, the methods described herein can be used to treat domesticated animals and/or pets. A subject can be male or female. A subject can be one who has been previously diagnosed with or identified as suffering from or having a disease or disorder needing treatment, but need not have already undergone treatment. For example, the subject can be one who has been previously diagnosed with or identified as suffering from or having a microbial infection, e.g., a fungal infection.

In some embodiments of any one of the aspects, the subject is human.

The term "disorder" or "disease" used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection.

In some embodiments of any one of the aspects, the disorder or disease is a cancer. As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably. As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments of any one of the aspects described herein, the disease or disorder is a wound. As used herein, the term "wound" refers to physical disruption of the continuity or integrity of tissue structure caused by a physical (e.g., mechanical) force, a biological (e.g., thermic or actinic force), or a chemical means. In one embodiment, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, burns, and biting, and other types of wounds. In some embodiments, the term "wound" encompasses ulcerations (e.g., ulcers), or ulcers of the skin. In some embodiments, the term "wound" also includes surgical wounds.

The wound can be acute or chronic. As used herein, the term "chronic wound" refers to a wound that does not fully heal even after a prolonged period of time (e.g., two to three months or longer). Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multi-factorial. As the normal responses of resident and migratory cells during acute injury become impaired, these wounds are characterized by a prolonged inflammatory response, defective wound extracellular matrix (ECM) remodeling and a failure of re-epithelialization.

The wound can be an internal wound, e.g. where the external structural integrity of the skin is maintained, such as in bruising or internal ulceration, or external wounds, particularly cutaneous wounds, and consequently the tissue can be any internal or external bodily tissue. In some embodiment the tissue is skin (such as human skin), i.e. the wound is a cutaneous wound, such as a dermal or epidermal wound.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex.

In some embodiments, the wound is selected from the group consisting of cuts and lacerations, surgical incisions or wounds, punctures, grazes, scratches, compression wounds, abrasions, friction wounds (e.g. nappy rash, friction blisters), decubitus ulcers (e.g. pressure or bed sores), thermal effect wounds (burns from cold and heat sources, either directly or through conduction, convection, or radiation, and electrical sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g. psoriasis and eczema, stomach or intestinal ulcers, oral wounds, including a ulcers of the mouth, damaged cartilage or bone, amputation wounds, corneal lesions, and any combinations thereof.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. Salts, esters, and other pharmaceutically acceptable forms of such compounds are also included. In some embodiments of any one of the aspects described herein, the small molecule is a therapeutic agent.

A "protein," "peptide," or "polypeptide" comprises a polymer of amino acid residues linked together by peptide bonds. The terms refer to proteins, polypeptides, and peptides of any size, structure, or function. Typically, a protein or peptide will be at least three amino acids long. A protein may refer to an individual protein or a collection of proteins. Proteins, peptides, and polypeptides can contain natural amino acids and/or non-natural amino acids (i.e., compounds that do not occur in nature can be incorporated into a polypeptide chain). A protein or polypeptide may be a single molecule or may be a multi-molecular complex. A protein or polypeptide may be a fragment of a naturally occurring protein or peptide. A protein may be naturally occurring, recombinant, synthetic, or any combination of these.

The term "nucleic acid" (also referred to as "polynucleotides" or "oligonucleotides") refers to a series of nucleotide bases (also called "nucleotides") in DNA and RNA, and refers to any chain of two or more nucleotides. A nucleotide sequence typically carries genetic information, including the information used by cellular machinery to make proteins and enzymes. These terms include double- or single-stranded genomic and cDNA, RNA, any synthetic and genetically manipulated polynucleotides, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims. The invention is further illustrated by the following examples, which should not be construed as further limiting.

Examples

An exemplary nanofiber scaffold was prepared in this study that is capable of encapsulation and release of hydrophilic cargo (e.g., protein or small molecule drug) from its pores and small molecule or hydrophobic cargo in its fibers. It releases the cargo slowly over time according to the engineering parameters described herein. The scaffold is mechanically stable and easily sutured while allowing for a diverse range of potential cargos (e.g. protein, peptide, small molecule, nanoparticle). The invention can be used in any application requiring the release of drug cargo from an implantable biomaterial. Cargo can be hydrophobic or hydrophilic, and mesh loading can be scaled to large or small quantities for release.

The data shown herein relates to the use of this surgical mesh system to activate various inducible CAR T cells, one of many potential applications. As a non-limiting example, the SUPRA CAR T cell system is used (FIG. 1), developed in the Wong laboratory, along with the NS3 CAR T cell system (FIG. 2), each of which have been combined with our novel surgical mesh device developed in the Grinstaff laboratory (FIG. 3) to achieve spatiotemporal control and increased CAR T activity. Briefly, a CAR, called a "zip-CAR", is expressed on the surface of a patient's T cell with an extracellular leucine zipper component. An orthogonal, matching leucine zipper is attached at the C-terminus to an scFv against the antigen of choice. This protein is used as a model cargo to demonstrate the utility of this novel biomaterial mesh, notably, maintaining stability of the protein without denaturation for at least 50 days when stored in phosphate buffered saline at physiologic pH and temperature. This protein, called a zipFv, spontaneously forms nanoparticles with a custom polymer, polyamidosaccharide (PAS), which stabilizes the protein through the mesh fabrication process. The nanoparticles are dispersed in a 1% chitosan solution, which is dropcast onto a polycaprolactone (PCL) electrospun nanofiber mesh similar to many surgical meshes in use today. The chitosan and zipFv-nanoparticles fill the pores of the mesh and are released slowly over time in physiologic conditions. Notably, while the PAS NPs increase the stability of proteins embedded in the mesh, they are not necessary for loading of proteins into the nanofiber mesh.

Figure 4:
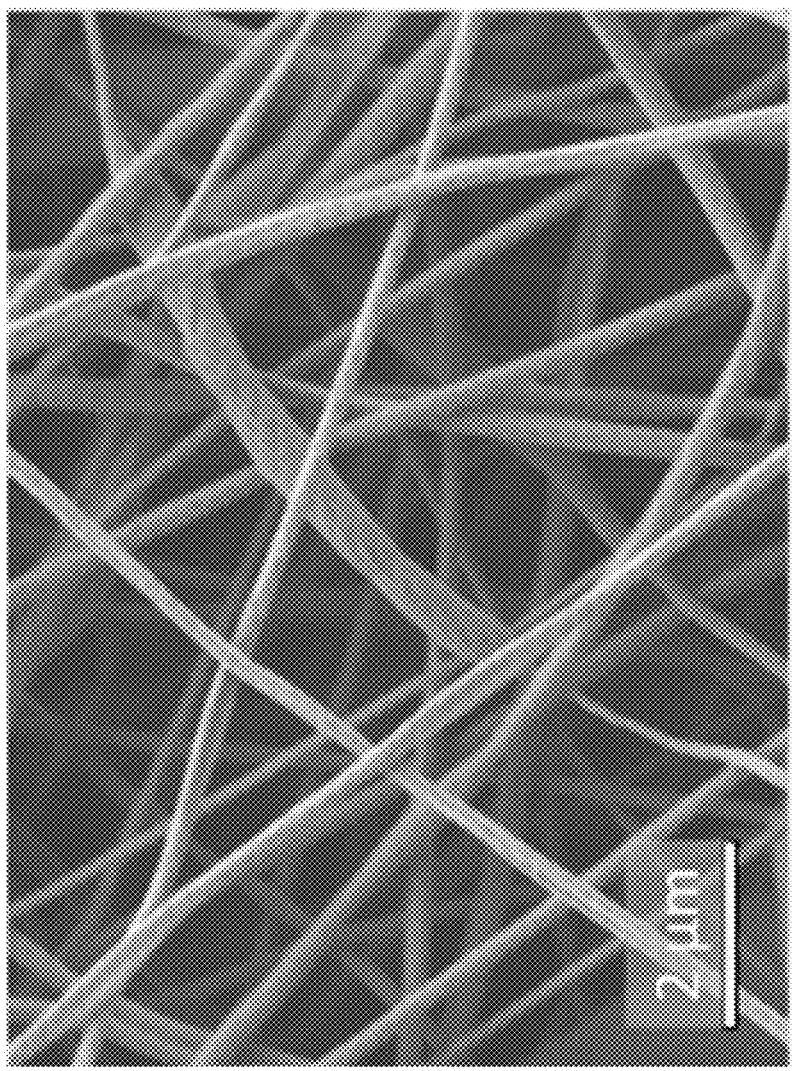
FIG. 4 shows PCL meshes made by electrospinning produce nanofibers approximately 100 nm in diameter. 5000×, bare fibers

The basic properties of the mesh delivery system are designed and characterized in vitro as it relates to the SUPRA CAR system, the NS3 CAR system, and release of doxorubicin from the mesh. The electrospinning protocol was optimized to synthesize fibers approximately 100 nm (actual: 123 f 22 nm) in diameter and randomly oriented (FIG. 4). The electrospinning parameters are described in Table 1.

TABLE 1

Electrospinning parameters associated with the nanofiber mesh

| Parameter | Value |
| --- | --- |
| Polymer | Polycaprolactone (MW 40,000) |
| Solvent | Chloroform:Dimethylformamide (70:30) |
| Polymer % (W/V) | 27 |
| Pump speed (ml/hour) | 0.9 |
| Volume per mesh (ml) | 1 |
| Area of mesh (cm$^2$) | 49 |
| Voltage (kV) | 27.5 |
| Target distance (cm) | 13 |

Figure 5B:
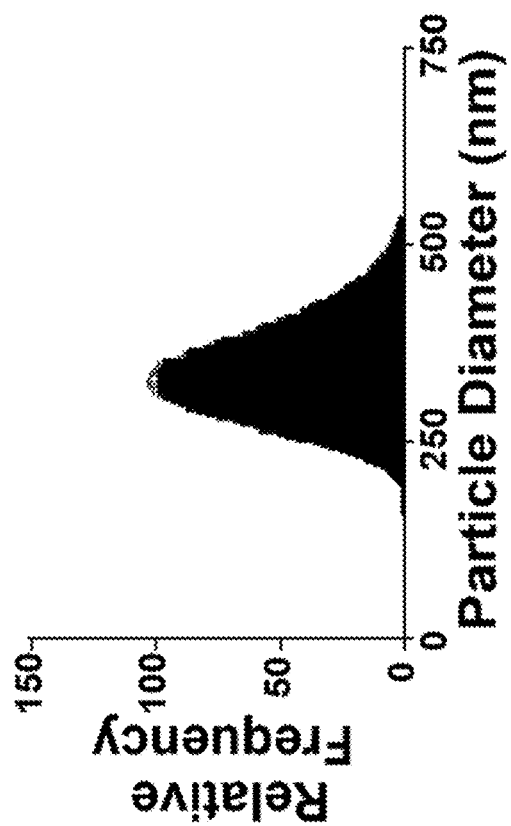
FIG. 5B shows ZipFv-PAS spontaneously formed aggregate nanoparticles (NPs) are approximately 300 nm in diameter and form FIG. 6A examines chitosan matrix filling the pores of the nanofiber mesh.
Figure 5A:
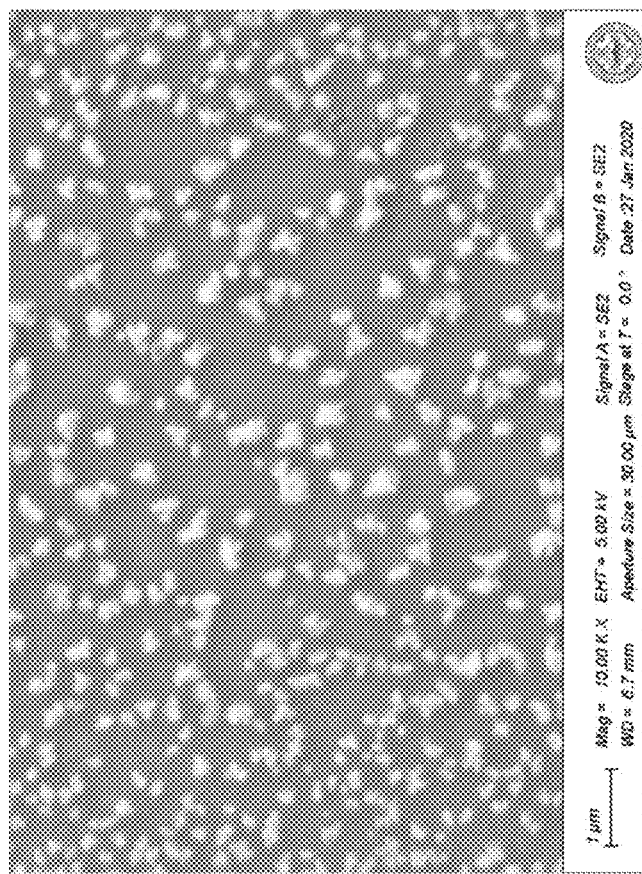
FIG. 5A is a photograph showing ZipFv-PAS spontaneously formed aggregates of negatively charged protein and positively charged NPs together.
Figure 6A:
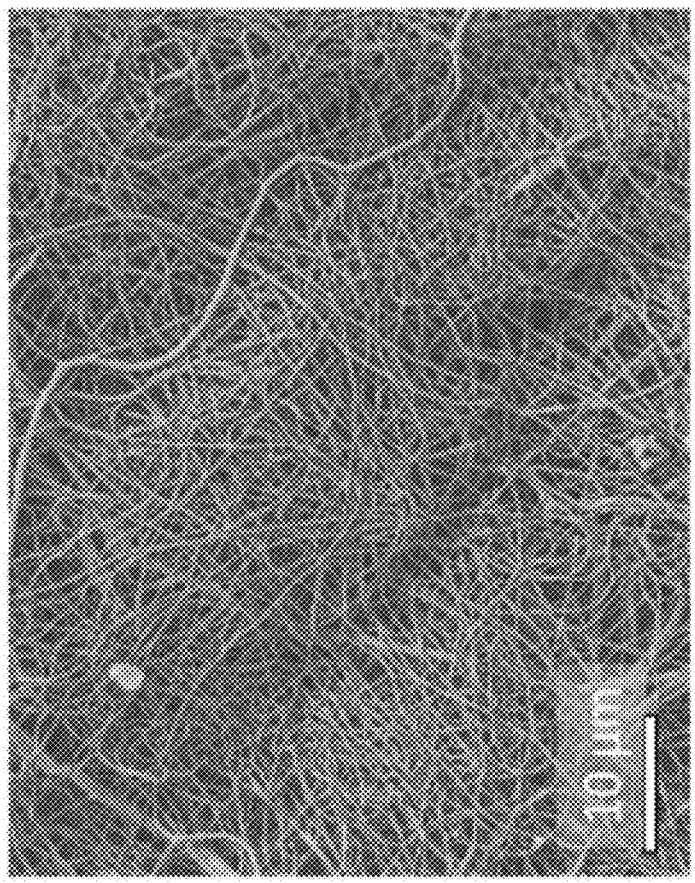
FIG. 6B shows, with the addition of poloxamer 407, sold under the tradename PLURONIC® F-127), chitosan into the matrix and coats individual nanofibers and fills the pores. The chitosan matrix can contain proteins, NPs, or other hydrophilic cargo.
Figure 6B:
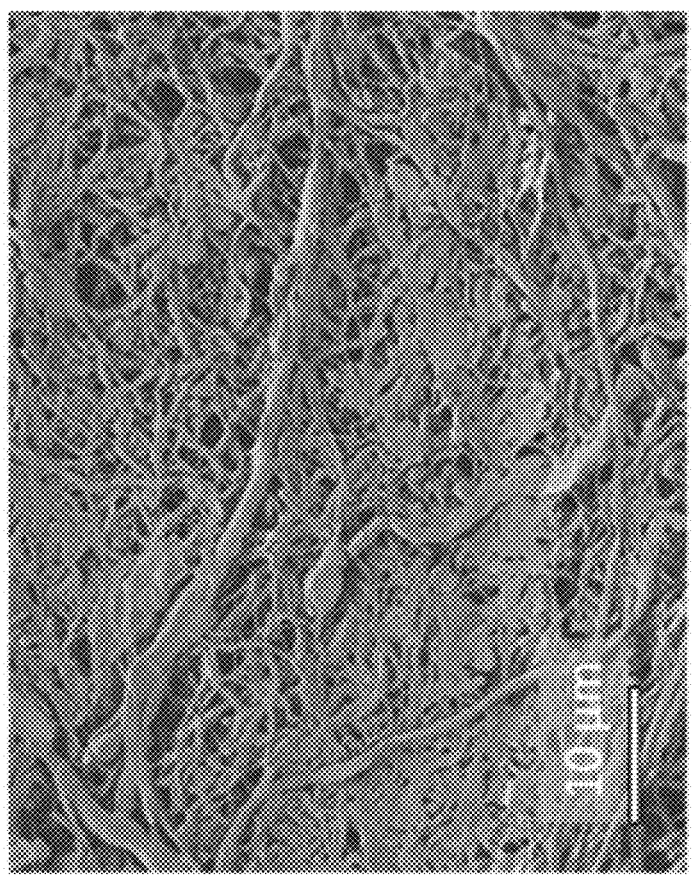
Figure 7B:
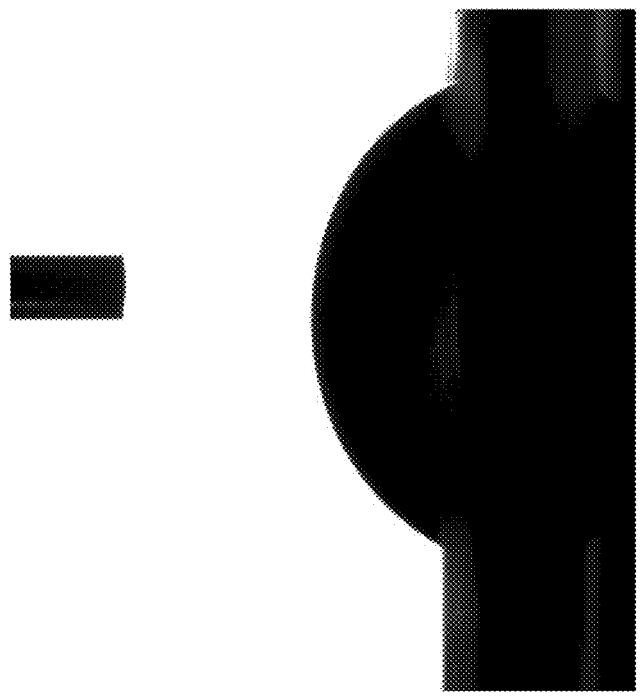
FIG. 7B shows the hydrophilic nature of the chitosan matrix after application (right).
Figure 7A:
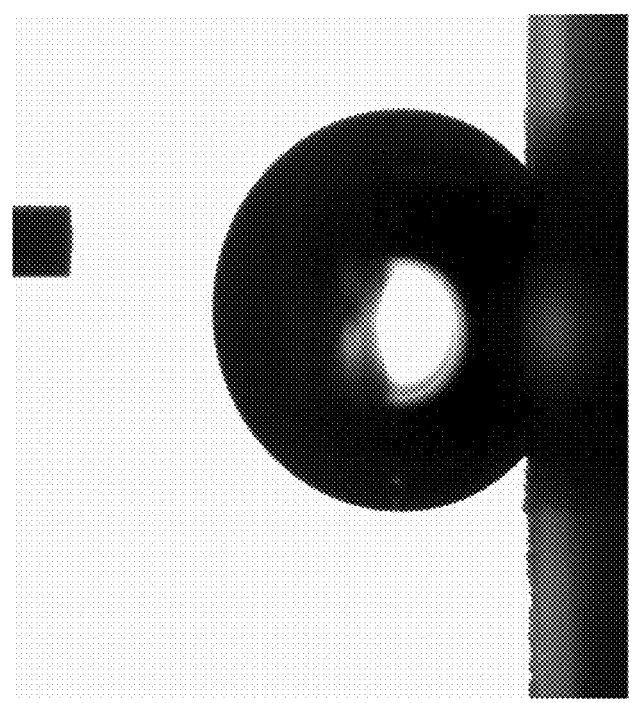
FIG. 7A shows the contact angle of the mesh with and without chitosan, demonstrating the hydrophobicity of the nanofiber matrix (left).
Figures 8A, 8B:
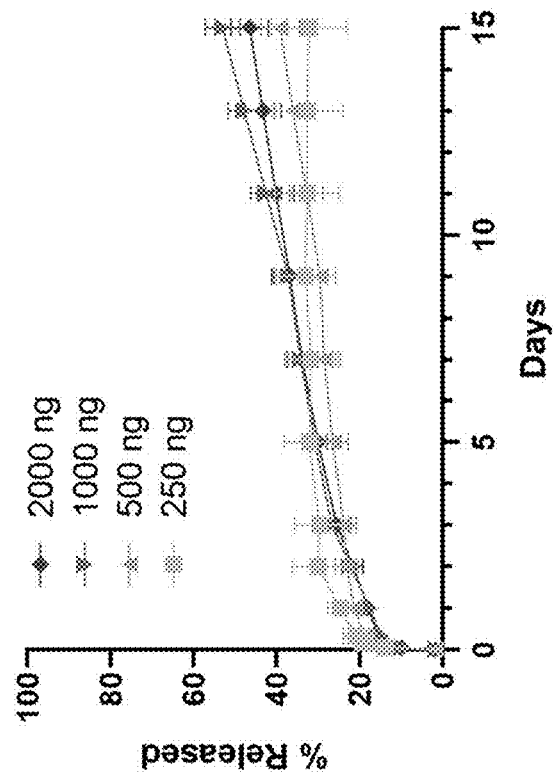
FIG. 8A depicts release characteristics of the mesh. When loaded with 250-2000 ng of zipFv protein cargo, meshes release cargo over a period of at least 15 days (left).
FIG. 8B shows the release is proportional to loading (right).
Figure 10:
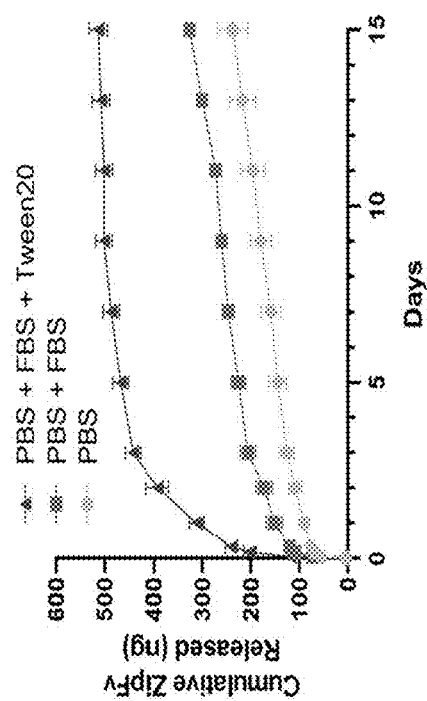
FIG. 10 shows releasing in phosphate buffered saline (PBS) without fetal bovine serum (FBS) decreases the release of protein from the mesh. Releasing in PBS with FBS and Tween20 increases release rate of protein from the mesh.
Figure 9:
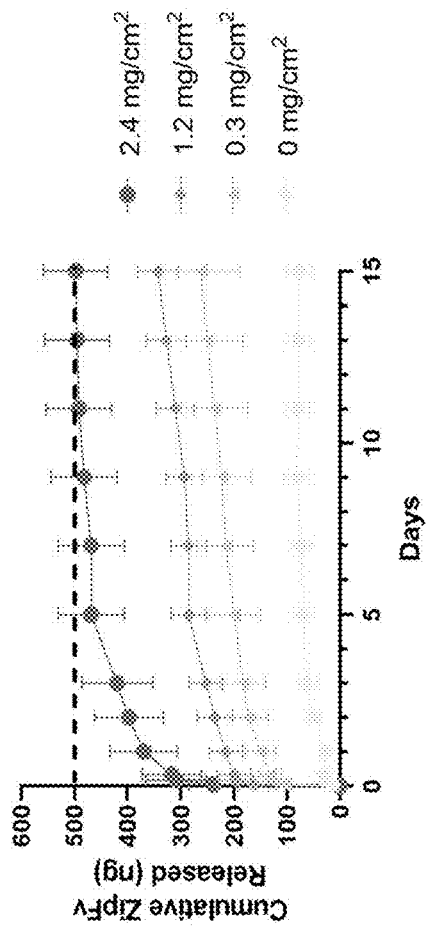
FIG. 9 examines varying the chitosan density modulates the release rate of protein from the mesh.
Figure 11:
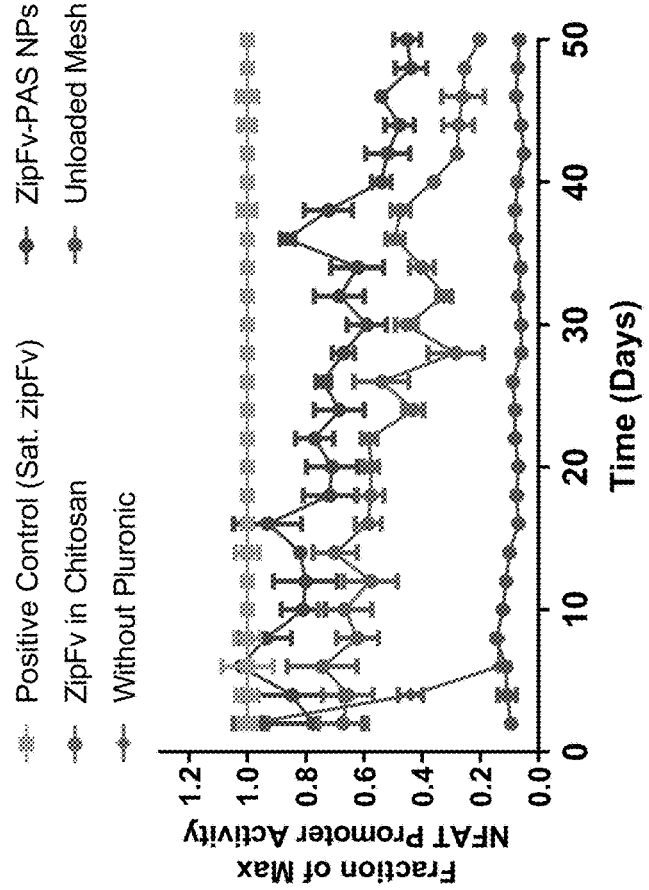
FIG. 11 shows the extended release of zipFv from nanofiber meshes allows for activation. Without the addition of poloxamer, sold under the tradename PLURONIC™, penetration of the chitosan matrix into the mesh is insufficient and extended release is not maintained. Poloxamer, sold under the tradename PLURONIC™ allows for wetting of the mesh and pore filling by the chitosan matrix. Addition of PAS polymer allows for greater activation over time (blue). (n=3)

ZipFv, a negatively charged protein, spontaneously forms a nanoparticle (FIG. 5) with a custom polymer, a positively charged, synthetic polyamidosaccharide (PAS). When combined with a chitosan solution in DI water, 0.5% acetic acid (pH 5.2), and 0.1% poloxamer 407, sold under the tradename PLURONIC® F-127 to enhance wetting, the zipFv and chitosan seep into the pores of the nanofiber mesh and create a stable, biodegradable depot of zipFv protein (FIG. 6). Addition of poloxamer 407, sold under the tradename PLURONIC® F-127 was crucial for both penetration of the nanofiber buttress, which is naturally hydrophobic (contact angle: 107°) (FIG. 7), and for prolonged release of zipFv from the network. Release of zipFv was quantified via fluorescently tagged zipFv released from the meshes. Meshes can be loaded to various densities and exhibit similar release characteristics (FIG. 8). The mechanism of release is by adsorption to the fibers and subsequent wetting of the mesh, dictated by the hydrophilic nature of the pores. This is a novel release mechanism for protein cargo. When additional chitosan is added to the mesh, release is faster, demonstrating the ability to modulate protein release by modulating mesh hydrophilicity. Without chitosan, release is slow and plateaus after a few days (FIG. 9). The wetting mechanism is further supported by rapid release with addition of Tween20 to the release sink (FIG. 10). Without addition of poloxamer, sold under the tradename PLURONIC™, poor wetting leads to failure of the chitosan matrix to incorporate within the pores of the mesh. This leads to rapid release of zipFv and loss of adaptor protein, hence, CAR T cell function, within a single week. This finding was demonstrated by functional release (FIG. 11). Thus, integration of the chitosan matrix into the hydrophobic nanofiber network is a key component in controlling release, and addition of zipFv NPs enhance activity.

Figure 12:
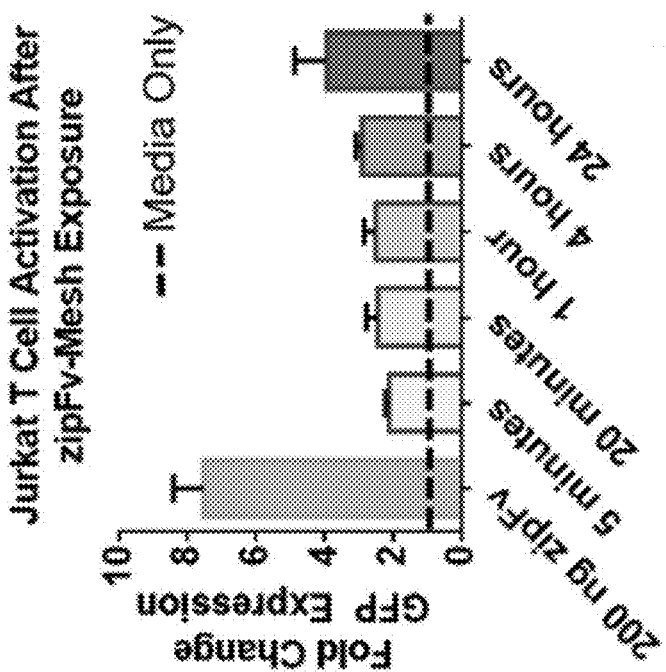
FIG. 12 shows over 24 hours, gradually more human epidermal growth factor receptor 2 (HER2)-targeted zipFv is released from the mesh and a greater level of jurkat zipCAR T cell activation is achieved over time in co-culture with HER2+ NALM6 cells (n=3).
Figure 13:
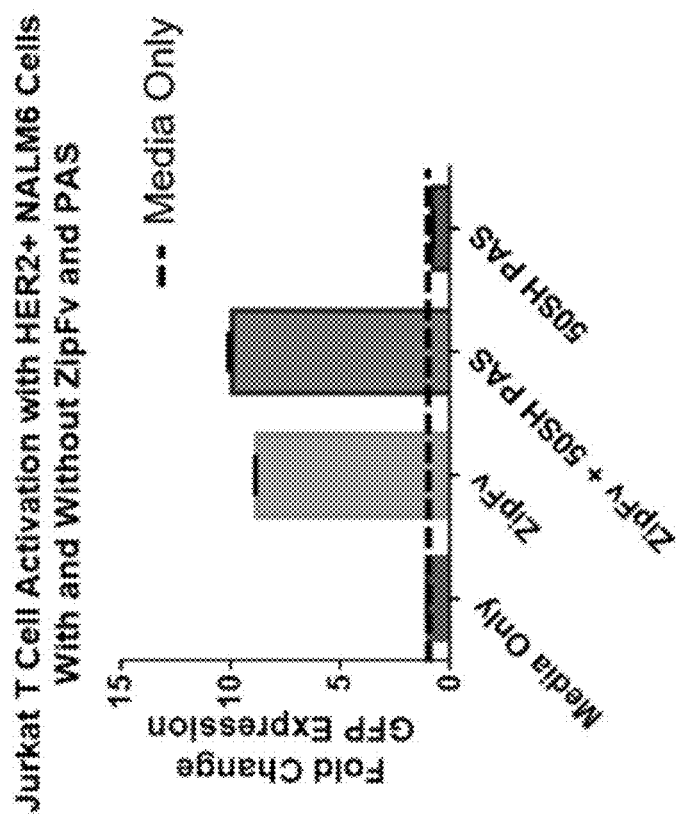
FIG. 13 depicts PAS polymer alone does not activate jurkat zipCAR T cells in co-culture with HER2+ Nalm6 cells and does not interfere with jurkat zipCAR T cell activation. (n=3).
Figures 14A, 14B:
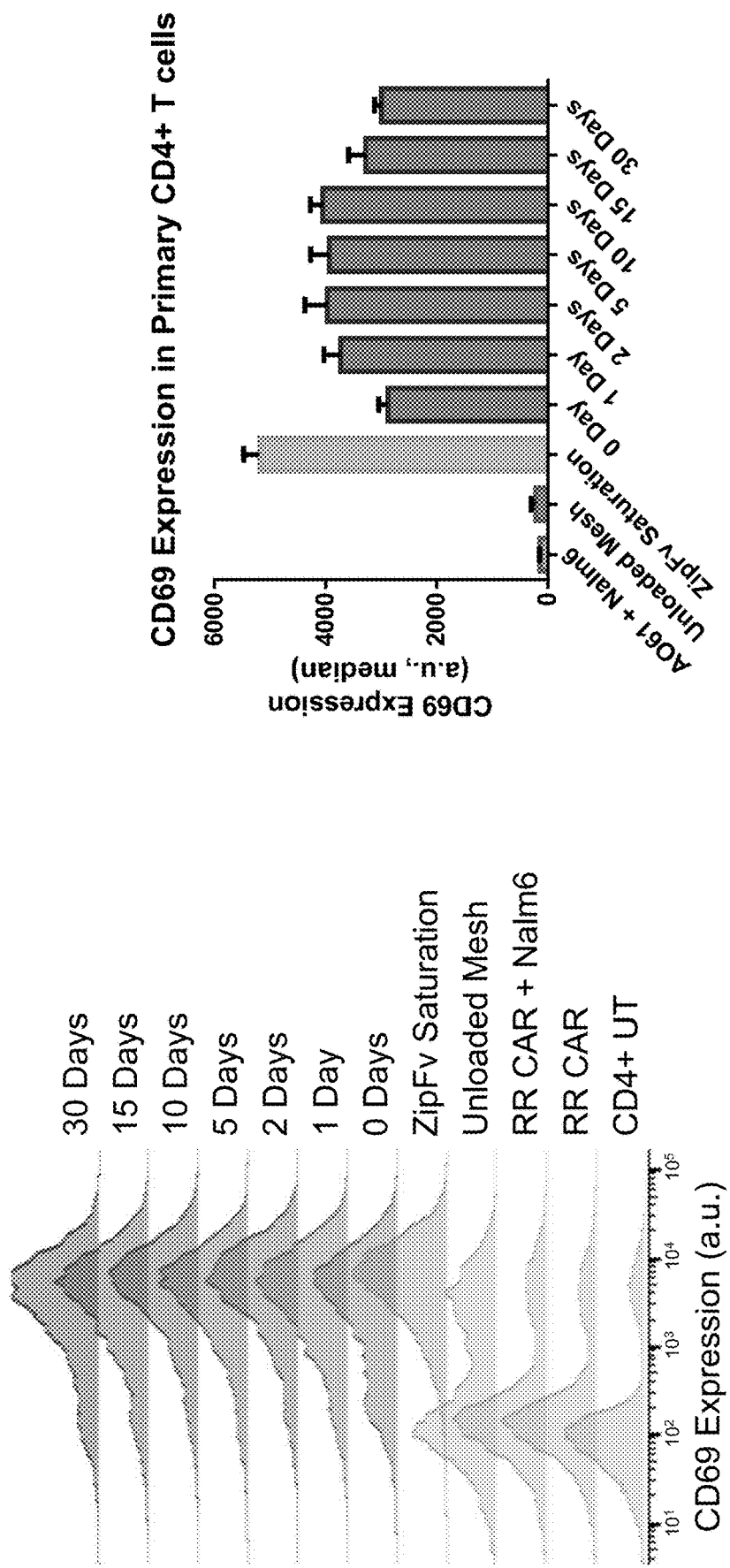
FIG. 14A-14B shows meshes activate primary T cells after 0, 1, 2, 5, 10, 15, or 30 days of release. CD69 expression levels are measured with flow cytometry as an early marker of T cell activation. (n=3).
Figure 15:
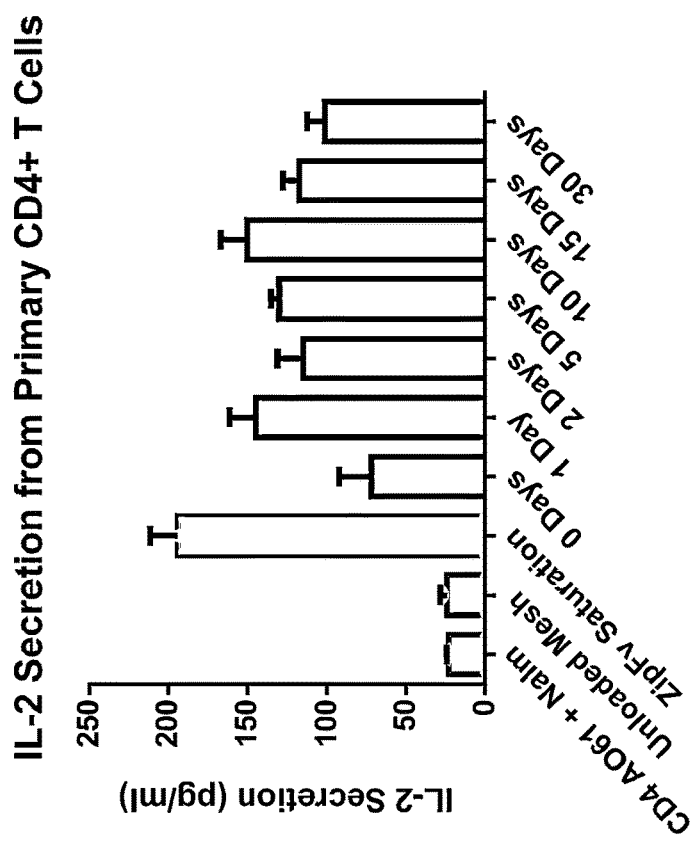
FIG. 15 shows exemplary meshes activate primary T cells after 0, 1, 2, 5, 10, 15, or 30 days of release. Interferon-gamma (IFN-γ) expression levels are measured with ELISA as a marker of T cell activation. (n=3).

Meshes were first characterized via their ability to induce activation in co-cultures of jurkat T cells transduced with zipCAR constructs over 24 hours (FIG. 12). Then, the functional release profile was characterized via the ability of meshes to induce CAR signaling when zipCAR-transduced jurkat T cells are co-incubated with the meshes and antigen expressing target cells (in this case NALM6 cells transduced with HER2). For 48 hours, meshes released HER2-targeted zipFv into a bath of media containing jurkat CAR T cells engineered with an NFAT-GFP reporter system, designed to allow for assessment of NFAT reporter activity, and NALM6 cells expressing HER2 as target cells. Every 48 hours the cells were assessed via flow cytometry for NFAT activity relative to zipFv added directly to the well at a maximal dose (FIG. 13). The meshes were washed and new cells were incubated with the meshes. This process was repeated until the meshes were no longer releasing zipFv in sufficient quantity. This experiment was repeated, the second time comparing the original mesh architecture with a new design that utilized zipFv formed into nanoparticles with PAS as described above. As can be seen in FIG. 14, nanoparticle formation allows for a longer release time and greater activation of jurkat CAR T cells. PAS does not induce any NFAT promoter activity on its own (FIG. 15) and NFAT promoter activity is consistently higher in the meshes with PAS NPs.

Figure 16:
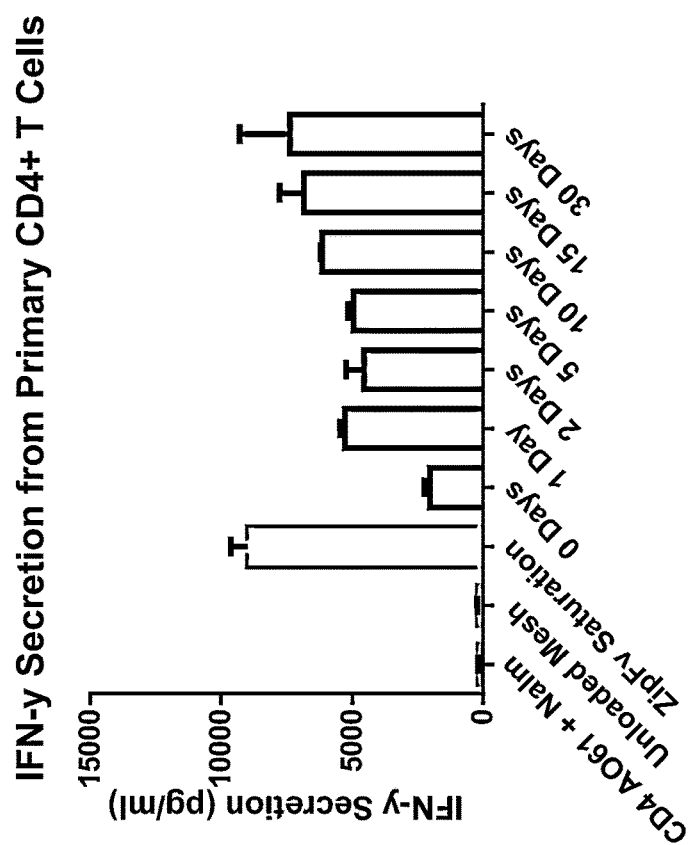
FIG. 16 shows meshes activate primary T cells after 0, 1, 2, 5, 10, 15, or 30 days of release. IL-2 expression levels are measured with ELISA as a marker of T cell activation. (n=3)

The meshes were evaluated for excitation and cytokine release from primary CD4+ T cells collected from anonymous blood donors at Boston Children's Plasma Donation Center. Meshes eluted zipFv in release buffer for a specified time interval, then they were washed and co-incubated with CD4+ zipCAR T cells and HER2+ NALM6 target cells for 24 hours. Cells were assessed for CD69 expression via flow cytometry (FIG. 14), IFN-γ release via ELISA (FIG. 15), and IL-2 release via ELISA (FIG. 16).

The above demonstrates the ability of these meshes to release proteins and nanoparticles through the chitosan, pore-filling encapsulation process. The meshes can also encapsulate hydrophobic molecules within the fibers themselves. This is demonstrated using grazoprevir encapsulated within the fibers, which is released to activate CAR T cells that are stabilized with grazoprevir. To demonstrate dosage control, these studies were done with grazoprevir loaded at 50, 100, 250, and 500 ng per 0.32 cm$^2$ (the size of one mesh for in vitro studies).

Figure 2:
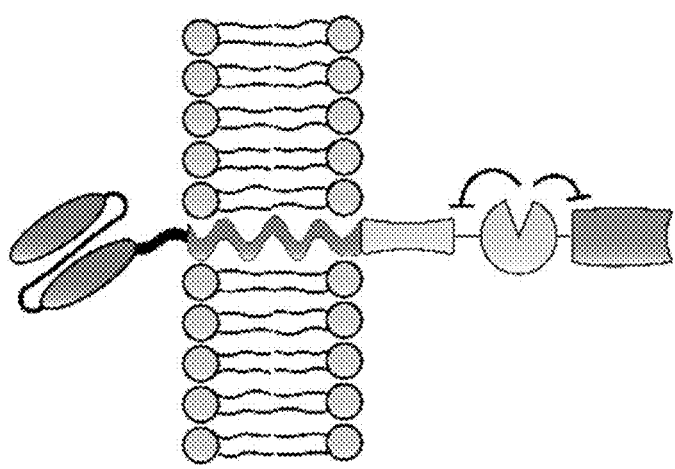
FIG. 2 shows the nonstructural protein 3 (NS3) CAR takes a small molecule input (grazoprevir) to inhibit self-cleavage of NS3 cut sites built into the receptor.
Figure 3:
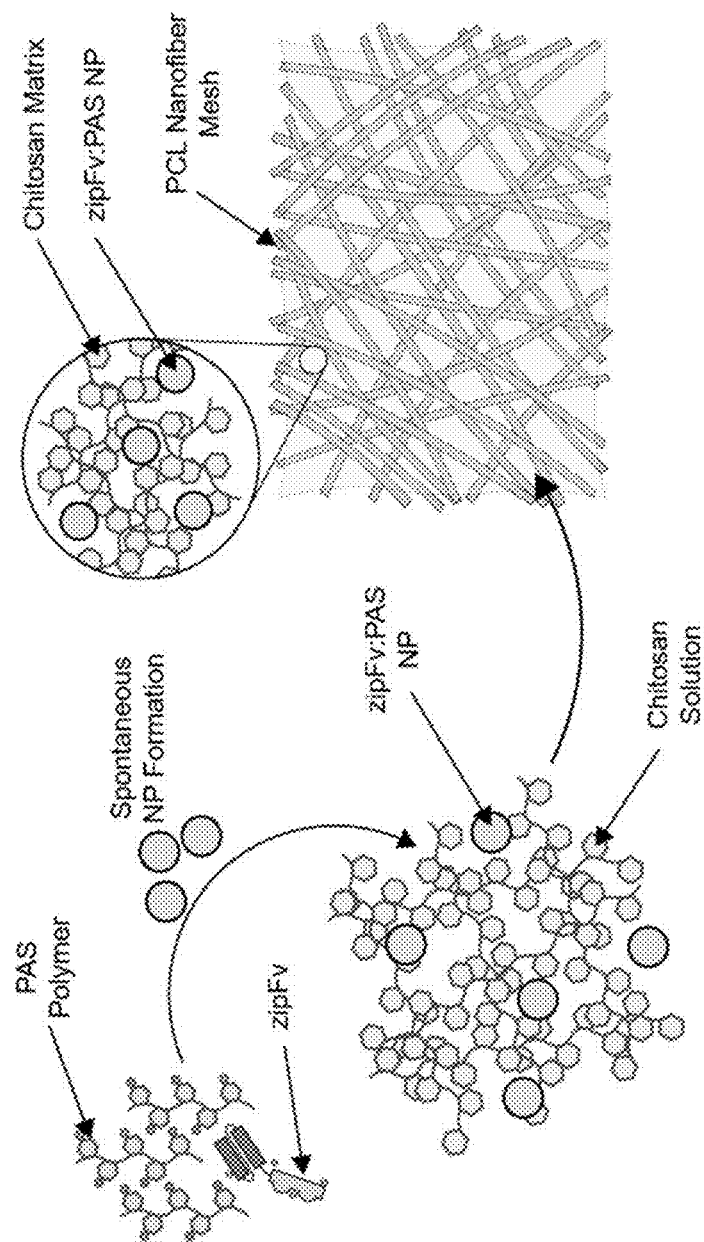
FIG. 3 depicts a surgical mesh structure. ZipFv and polyamidosaccharide (PAS) polymer spontaneously form nanoparticle aggregates, which can be dispersed in an aqueous solution of chitosan. This can be dropcast onto a polycaprolactone (PCL) nanofiber mesh fabricated through electrospinning.
Figure 17:
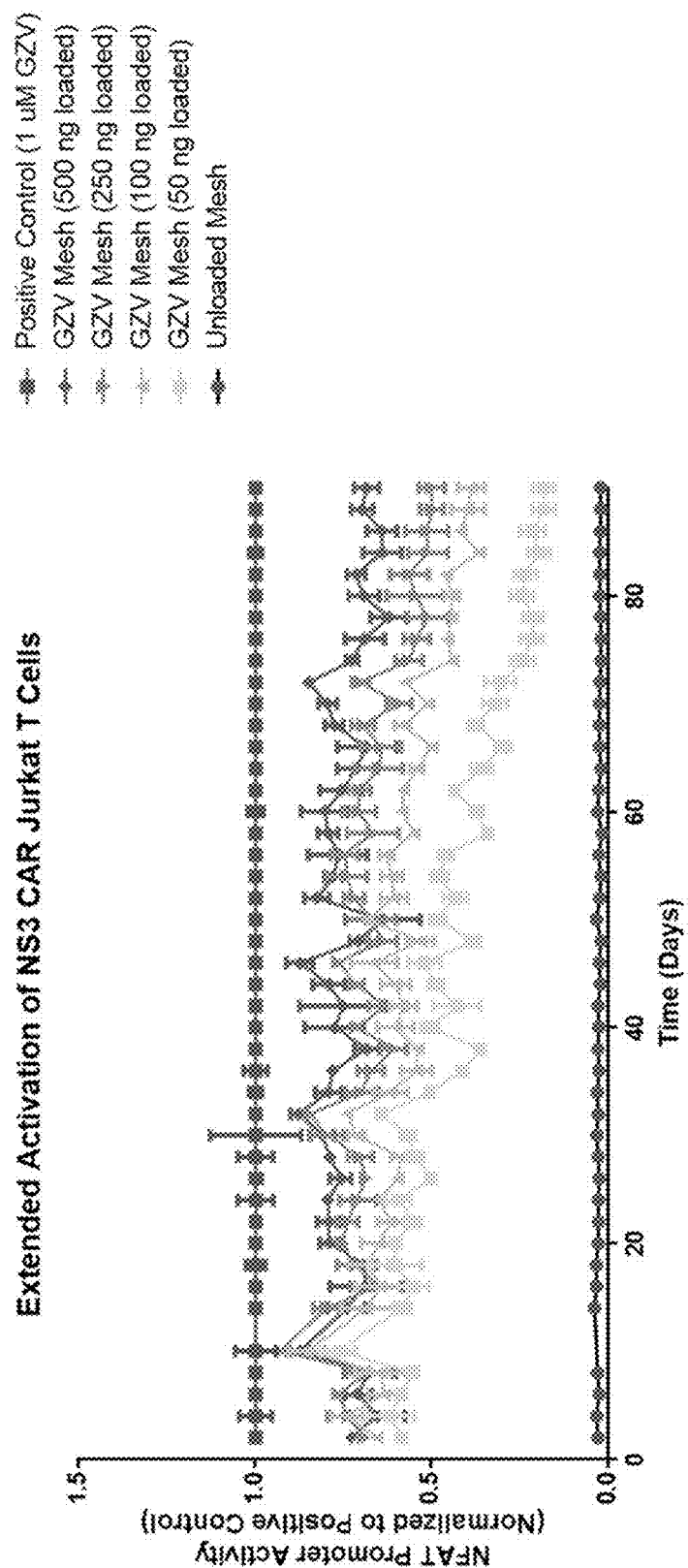
FIG. 17 depicts NFAT-GFP expression levels over 90 days of jurkat CAR T cells that require grazoprevir for CAR activity. Top line is positive control (1 uM of grazoprevir added). Pink lines are grazoprevir-loaded meshes as indicated. Bottom line is meshes not loaded with grazoprevir. All values normalized to the positive control (value of 1.0). (n=3)
Figure 18:
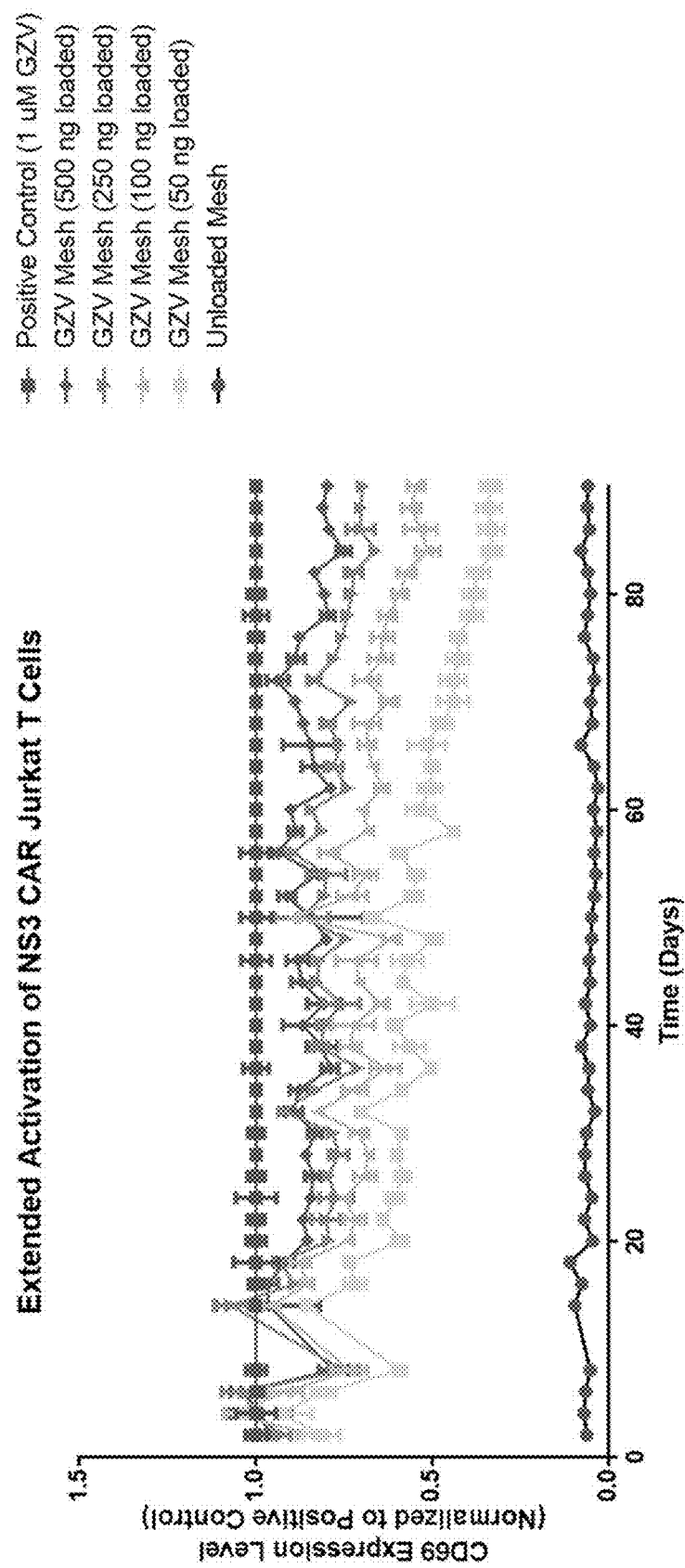
FIG. 18 depicts CD69 expression levels over 90 days of jurkat CAR T cells that require grazoprevir for CAR activity. Top line is positive control (1 uM of grazoprevir added). Pink lines are grazoprevir-loaded meshes as indicated. Bottom line is meshes not loaded with grazoprevir. All values normalized to the positive control (value of 1.0). (n=3)

The meshes were immersed in co-cultures of HER2+ NALM6 cells with grazoprevir-dependent HER2-targeted CAR T cells from FIG. 2. These cells are engineered with the same NFAT-GFP reporter system as those mentioned above. These cells exhibit no CAR activity in the absence of grazoprevir. All CAR activity would then be derived from grazoprevir released from the meshes into the culture media. FIG. 17 shows the NFAT-GFP response of jurkat CAR T cells over time. T cells and NALM6 cells were analyzed every 2 days, meshes were washed, and new cells were added. On each replacement, 100,000 of each cell type was added in 200 ul of media on top of the meshes. FIG. 18 shows the same experiments analyzing CD69 expression levels in these cells.

Figure 19:
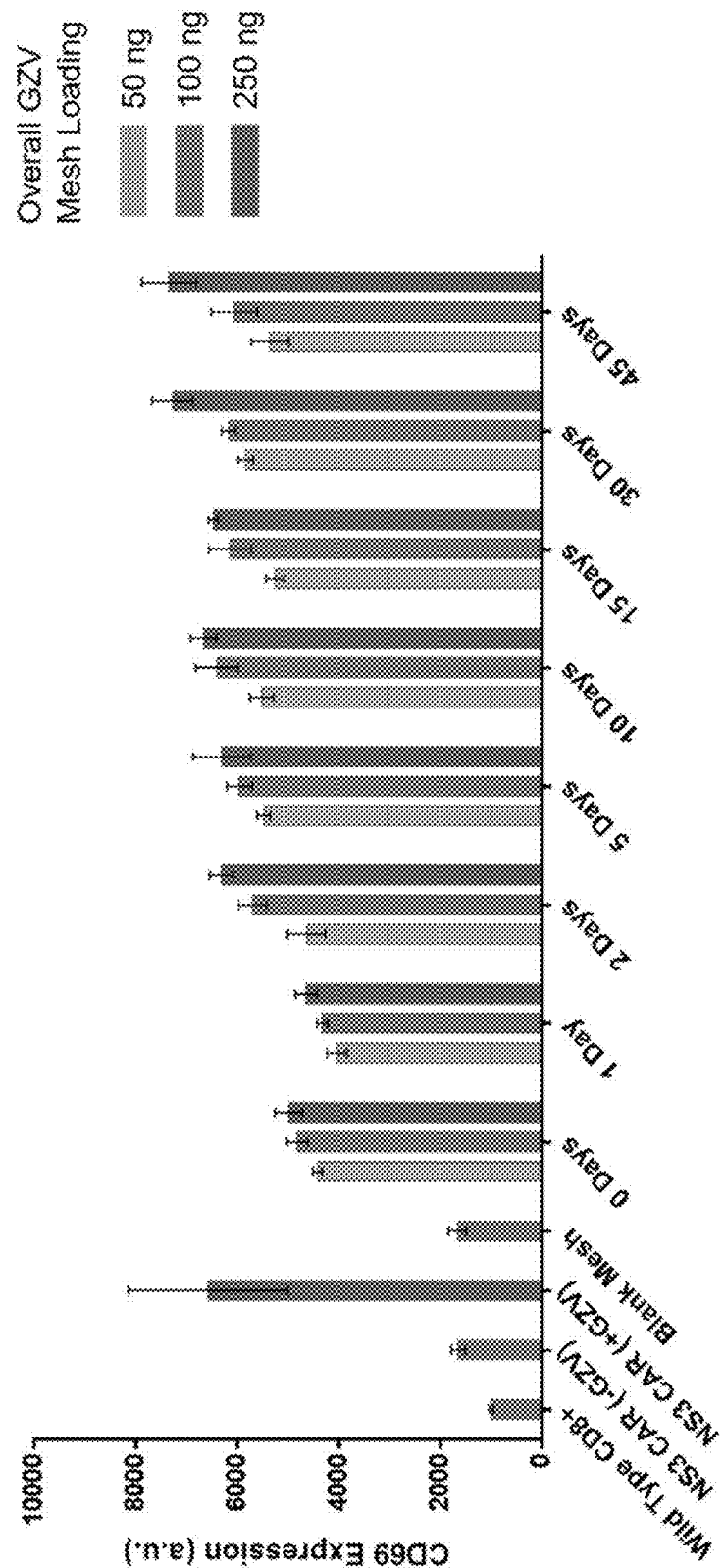
FIG. 19 depicts CD69 expression levels over 45 days of jurkat CAR T cells that require grazoprevir for CAR activity. (n=3)
Figure 20:
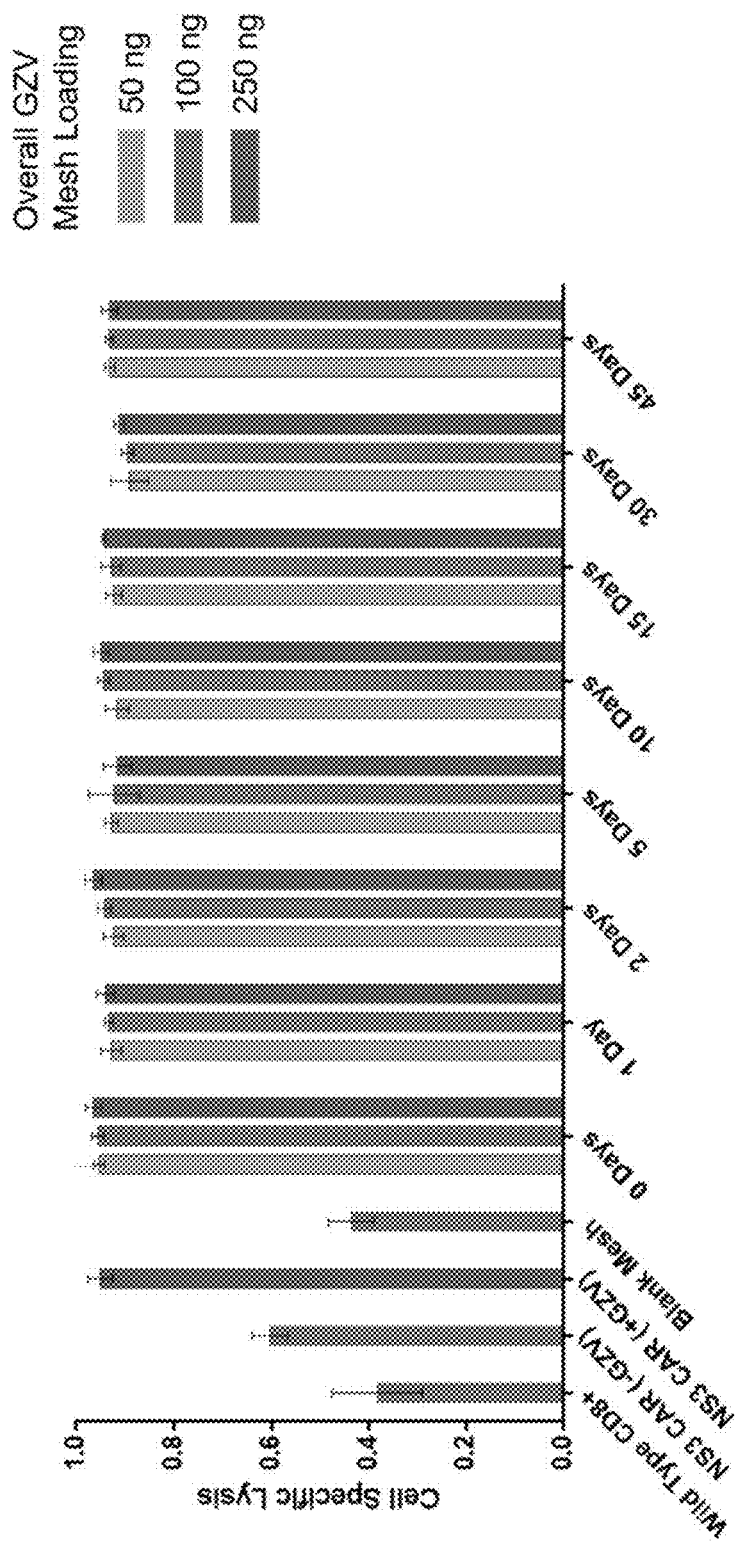
FIG. 20 shows HER2-positive NALM6 cell lysis over 45 days of jurkat CAR T cells that require grazoprevir for CAR activity. (n=3)
Figure 21:
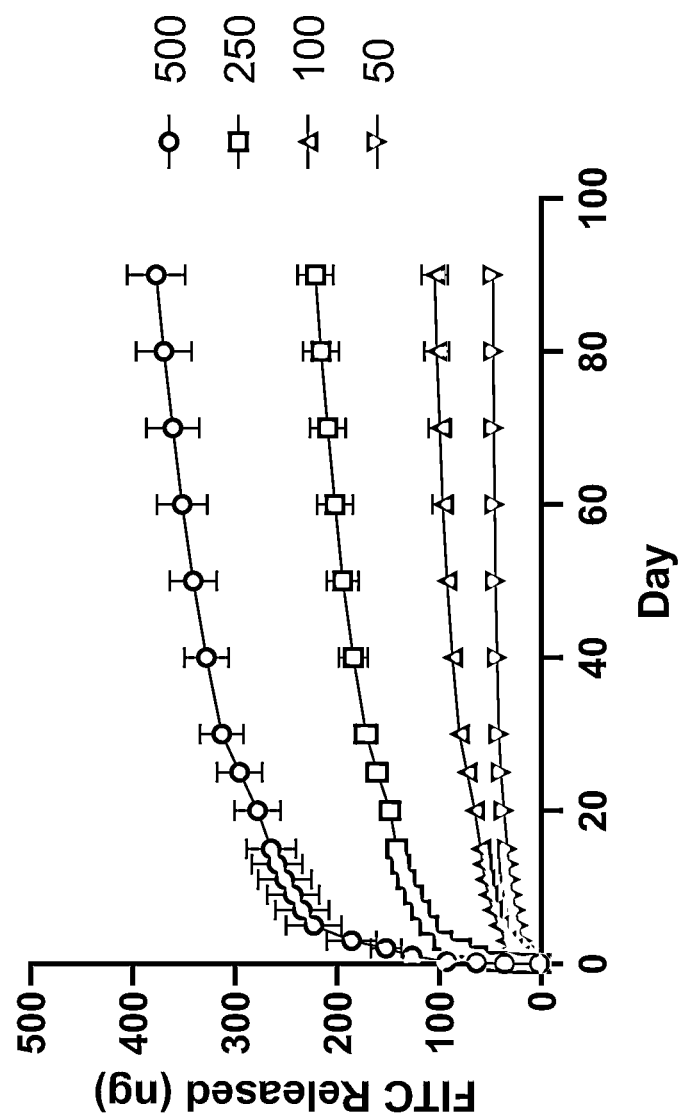
FIG. 21 depicts FITC (50-500 ng) released from the fibers over the course of 90 days. FITC was loaded in the mixture of the PCL solution similar to grazoprevir loaded meshes. (n=4)

When used with primary CD8+ HER2-targeted NS3 CAR T cells with the same grazoprevir-dependent CARs, the meshes were excited (CD69 expression) when co-cultured with the meshes and HER2-expression NALM6 cells (FIG. 19). Similarly, the cells incubated with the meshes lysed the target cells at maximal levels compared to cells that were directly supplied with a saturating dose of grazoprevir (FIG. 20). FIG. 21 demonstrates FITC release over 90 days, used as a model cargo with similar log P to grazoprevir (4.8 vs. 4.7). These experiments demonstrate the ability of the meshes to release functional cargo over time.

Figure 22:
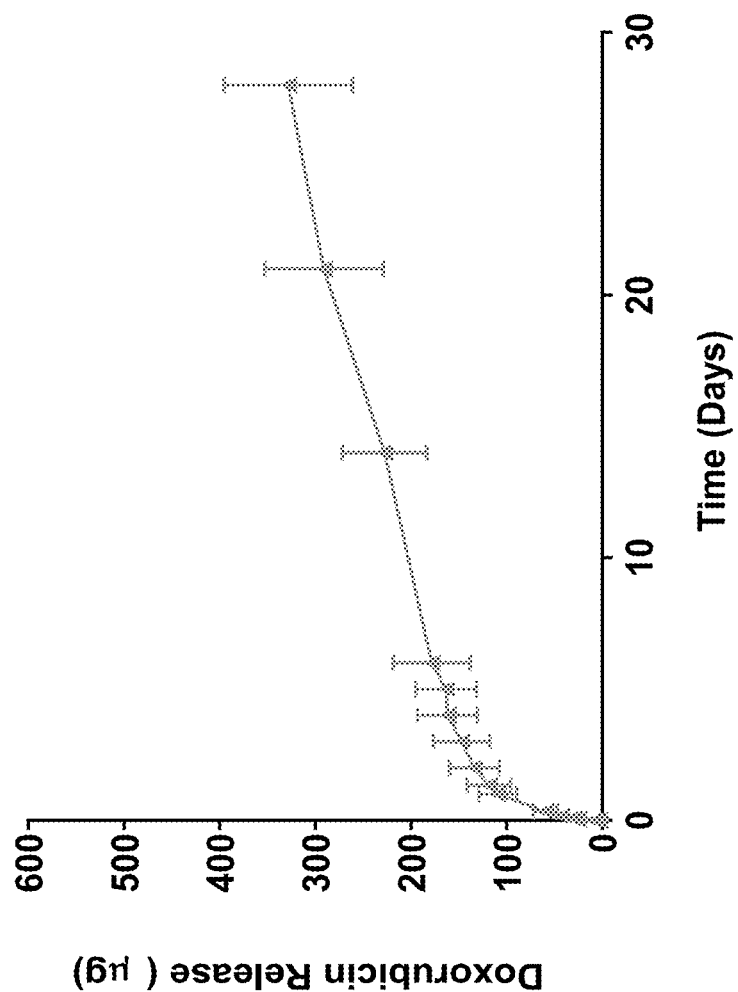
FIG. 22 shows doxorubicin (500 ug loaded) released from the fibers over the course of 28 days. Doxorubicin was loaded in the mixture of the PCL solution similar to grazoprevir loaded meshes. (n=3)

The meshes ability to release doxorubicin over time was characterized as a functional delivery method for chemotherapeutic drugs. The drugs, as shown in FIG. 22, release over several weeks to months in vitro.

The applications of the drug delivery composition and methods described herein are broad. The drug delivery composition can encapsulate a large variety of compounds, both small molecule, hydrophobic drugs and hydrophilic, protein therapeutics. This can be useful for many technologies related to drug delivery, particularly for applications that require installation of a surgical mesh (e.g. cancer resection, female urologic procedures, hernia surgery).

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

What is claimed is:

1. A drug delivery composition comprising:
   a. a scaffold comprising electrospun nanofibers of a first polymer and wherein the scaffold comprises a plurality of pores; and
   b. an active agent,
   wherein:
   (i) the active agent is present in a particle, the particle comprising the active agent, a second polymer and a third polymer, and wherein the particle is present in the pores of the scaffold; or
   (ii) the active agent is distributed inside the nanofibers or adsorbed on the nanofibers, and
   wherein the first polymer is hydrophobic,
   wherein the second polymer is hydrophilic, and
   wherein the third polymer is an amphiphilic polymer.

2. The drug delivery composition of claim 1, wherein the active agent is present in the particle comprising the active agent, the second polymer and third polymer.

3. The drug delivery composition of claim 1, wherein the particle is a nanoparticle.

4. The drug delivery composition of claim 1, wherein the particle comprises a fourth polymer and wherein the fourth polymer is different from the first, second or third polymer.

5. The drug delivery composition of claim 4, wherein the second and fourth polymer are different.

6. The drug delivery composition of claim 4, wherein the fourth polymer and the active agent self-assemble to form the particle.

7. The drug delivery composition of claim 4, wherein the fourth polymer is a polyamidosaccharide.

8. The drug delivery composition of claim 2, wherein the third polymer is a poloxamer.

9. The drug delivery composition of claim 2, wherein the second polymer is chitosan or the active agent is hydrophilic.

10. The drug delivery composition of claim 1, wherein the active agent is distributed inside the nanofibers or adsorbed on the nanofibers.

11. The drug delivery composition of claim 10, wherein the active agent is hydrophobic.

12. The drug delivery composition of claim 1, wherein the nanofibers have a diameter from about 50 nm to about 175 nm.

13. The drug delivery composition of claim 1, wherein the first polymer is polycaprolactone.

14. The drug delivery composition of claim 1, wherein the active agent is a small organic or inorganic molecule, peptide, polypeptide, oligonucleotide, polynucleotide, oligosaccharide, or polysaccharide, an extract made from a biological material.

15. The drug delivery composition of claim 1, wherein the active agent is conjugated with a targeting ligand.

16. The drug delivery composition of claim 15, wherein the targeting ligand is a first member of a binding pair.

17. The drug delivery composition of claim 16, wherein the binding pair is a pair of protein interaction domains.

18. The drug delivery composition of claim 17, wherein the protein interaction domains are leucine zipper domains.

19. The drug delivery composition of claim 1, wherein the active agent is an antibody or an antigen binding fragment thereof.

20. The drug delivery composition of claim 1, wherein the active agent is zipFV.

21. The drug delivery composition of claim 1, wherein the active agent is selected from the group consisting of anti-cancer agents, anti-inflammatory agents, antibiotic agents or antibacterial agents, anti-proliferatives, anti-migratory agents, anti-fibrotic agents, proapoptotics, anti-neoplastics, and immuno-suppressants.

22. The drug delivery composition of claim 1, wherein the active agent is present in a mixture comprising the active agent and a second polymer and a third polymer, and wherein:
   a. the first polymer is polycaprolactone;
   b. the second polymer is chitosan; and
   c. the third polymer is poloxamer 407.

23. The drug delivery composition of claim 22, wherein the active agent is comprised in a nanoparticle, and where the nanoparticle further comprises a polyamidosaccharide.

24. The drug delivery composition of claim 23, wherein the active agent is zipFV.

25. The drug delivery composition of claim 1, wherein the drug delivery composition provides sustained release of the active agent.

26. The drug delivery composition of claim 25, wherein sustained release of the active agent occurs for a period of at least ten days.

27. The drug delivery composition of claim 1, wherein the scaffold is a non-woven mesh.

28. The drug delivery composition of claim 1, wherein the drug delivery composition is in form of an implantable device.

29. A pharmaceutical composition comprising the drug delivery composition of claim 1 and a pharmaceutically acceptable carrier or excipient.

30. A method of delivering an active agent to a cell, the method comprising contacting a cell with the drug delivery composition of claim 1.

* * * * *